(12) United States Patent
Shin et al.

(10) Patent No.: US 12,173,074 B2
(45) Date of Patent: Dec. 24, 2024

(54) ANTI-C-MET AGONIST ANTIBODY AND USE THEREOF

(71) Applicants: SEOUL NATIONAL UNIVERSITY R&DB FOUNDATION, Seoul (KR); ABION INC., Seoul (KR)

(72) Inventors: Young Kee Shin, Seoul (KR); Ji Hye Lee, Seoul (KR); Young Deug Kim, Seoul (KR); Jun Young Choi, Seoul (KR)

(73) Assignees: SEOUL NATIONAL UNIVERSITY R&DB FOUNDATION, Seoul (KR); ABION INC., Seoul (KR)

( * ) Notice: Subject to any disclaimer, the term of this patent is extended or adjusted under 35 U.S.C. 154(b) by 711 days.

(21) Appl. No.: 17/299,086

(22) PCT Filed: Dec. 6, 2019

(86) PCT No.: PCT/KR2019/017242
§ 371 (c)(1),
(2) Date: Jun. 2, 2021

(87) PCT Pub. No.: WO2020/117017
PCT Pub. Date: Jun. 11, 2020

(65) Prior Publication Data
US 2022/0220207 A1    Jul. 14, 2022

(30) Foreign Application Priority Data

Dec. 7, 2018 (KR) .................. 10-2018-0157325

(51) Int. Cl.
*C07K 16/28* (2006.01)
*A61P 35/00* (2006.01)

(52) U.S. Cl.
CPC .......... *C07K 16/2863* (2013.01); *A61P 35/00* (2018.01); *C07K 2317/75* (2013.01); *C07K 2317/92* (2013.01)

(58) Field of Classification Search
CPC ............ C07K 16/2863; C07K 2317/75; C07K 2317/92; C07K 2317/622; C07K 2317/73; C07K 2317/76; A61P 35/00; G01N 2333/71; G01N 2333/82; G01N 33/6854; C12N 5/0655; C12N 5/0667; C12N 2501/12; C12N 2501/50; C12N 2506/1384

See application file for complete search history.

(56) References Cited

U.S. PATENT DOCUMENTS

| | | | |
|---|---|---|---|
| 9,394,367 | B2 | 7/2016 | Cheong et al. |
| 9,469,691 | B2 * | 10/2016 | Goetsch ............... A61K 31/517 |
| 9,493,739 | B2 | 11/2016 | Nam et al. |
| 2006/0134104 | A1 | 6/2006 | Dennis et al. |
| 2013/0089542 | A1 | 4/2013 | Lee et al. |
| 2014/0086914 | A1 | 3/2014 | Michaud et al. |
| 2014/0301989 | A1 | 10/2014 | Johnstone et al. |
| 2015/0291696 | A1 | 10/2015 | Goetsch et al. |

OTHER PUBLICATIONS

Gonzalez et al. (2016), A novel antagonist anti-cMet antibody with antitumor activities targeting both ligand-dependent and ligand-independent c-Met receptors. Int. J. Cancer, 139: 1851-1863. (Year: 2016).*
Matsumoto et al. (2017) Hepatocyte growth factor/MET in cancer progression and biomarker discovery. Cancer Sci, 108: 296-307. (Year: 2017).*
Sierra et al.. c-MET as a potential therapeutic target and biomarker in cancer. Therapeutic Advances in Medical Oncology. 2011; 3(S1):S21-S35. (Year: 2011).*
International Search Report and Written Opinion dated Mar. 24, 2020, from International Application No. PCT/KR2019/017242, 16 pages.

* cited by examiner

*Primary Examiner* — Julie Wu
*Assistant Examiner* — Amber K Faust
(74) *Attorney, Agent, or Firm* — Meunier Carlin & Curfman LLC

(57) ABSTRACT

The present invention relates to an anti-c-Met agonist antibody and use thereof, and more particularly, to an agonist antibody or fragment thereof that specifically binds to a human-derived c-Met protein, to a method for producing the same, to c-Met specific detection method using this, to a composition for preventing or treating cancer comprising the same, to a composition for inducing stem cell differentiation, and a culture medium for stem cells. The method of the present invention can be usefully used for detecting c-Met antibodies, inducing stem cell differentiation using the antibody, and treating or preventing cancer.

11 Claims, 17 Drawing Sheets

Specification includes a Sequence Listing.

FIG. 2

ANTI-C-MET AGONIST ANTIBODY AND USE THEREOF

TECHNICAL FIELD

This application is a national phase application filed under 35 U.S.C. § 371 of PCT International Application No. PCT/KR2019/017242, filed on Dec. 6, 2019, which claims priority to Korean Patent Application No. 10-2018-0157325 filed on Dec. 7, 2018, and the entire specifications of which are incorporated herein by reference in their entireties.

The present invention relates to an anti-c-Met agonist antibody and use thereof, and more particularly, to an agonist antibody or fragment thereof that specifically binds to a human-derived c-Met protein, to a method for producing the same, to c-Met specific detection method using this, to a composition for preventing or treating cancer comprising the same, to a composition for inducing stem cell differentiation, and a culture medium for stem cells.

BACKGROUND OF THE INVENTION c-Met is a representative RTK (Receptor Tyrosine Kinase) present on the cell surface. By binding with its ligand, HGF/SF (Hepatocyte Growth Factor/Scattering Factor), it is not only promotes intracellular signaling to promote cell growth, but is also overexpressed in many types of cancer cells, so that it is widely involved in cancer development, cancer metastasis, cancer cell migration, cancer cell penetration, and formation of new blood vessels. In addition, as the name of the ligand implies, c-Met signaling through HGF/SF is a representative protein in the early stages of cancer metastasis that causes scattering by weakening cell-cell contact of almost all types of epithelial tumors (Nat Rev Cancer. 2012) January 24; 12 (2): 89-103). In particular, it is well known that hypoxiaresponse elements exist in the upstream of the c-Met gene, and the expression of the gene is increased in oxygen deprivation (Oral Oncol. 2006 July; 42 (6): 593-8). In addition, since c-Met contributes to the various stages of cancer development from initiation to progression through metastasis, c-Met and its ligand HGF have been leading candidates for targeted cancer therapy (Comoglio et al. 2008. Nat Rev Drug Discov 7:504]; [Knudsen and Vande Woude 2008. Curr Opin Genet Dev 18:87]). In particular, as c-Met is known to be involved in drug resistance in the mechanism of action of previously known anticancer drugs, the importance of c-Met is being recognized more and more for personalized treatment, and c-Met has become a target molecule that many pharmaceutical companies are paying attention to in relation to anticancer drugs.

In recent years, antibodies to c-Met have been developed as anticancer agents as antagonists. But there are required the development of a c-Met antibody that it can specifically bind to c-Met with higher affinity, and it is unlikely to induce an immune response when administered in the body as consisting of human-derived sequences, and it exhibits more diverse activities.

DETAILED DESCRIPTION OF THE INVENTION

Technical Problem

Accordingly, the present inventors have made diligent efforts to develop antibodies that target c-Met and exhibit various physiological activities. As a result, in order to target c-Met, the present invention was completed by confirming that a human antibody consisting of a human-derived complementarity determining region (CDR) and a framework region (FR) that specifically binds to c-Met exhibits similar activity to HGF, and that it can function as an agonist antibody that induces signal transduction by binding with c-Met, a cell surface molecule.

Accordingly, an object of the present invention is to provide an agonist antibody or fragment thereof that specifically binds to a human-derived c-Met protein.

Another object of the present invention is to provide a polynucleotide encoding the antibody or fragment thereof, a vector, and a cell transformed with the vector.

Another object of the present invention is to provide a method for producing an agonist antibody or fragment thereof that binds to human c-Met and a method for specific detection of c-Met.

Another object of the present invention is to provide a pharmaceutical composition for preventing or treating cancer comprising the antibody or fragment thereof as an active ingredient.

In addition, another object of the present invention is to provide a pharmaceutical composition for prevention or treatment consisting of the antibody or fragment thereof.

In addition, another object of the present invention is to provide a pharmaceutical composition for preventing or treating cancer essentially consisting of the antibody or fragment thereof.

Another object of the present invention is to provide a composition for inducing stem cell differentiation comprising the antibody and a culture medium for stem cells comprising the same.

Another object of the present invention is to provide a composition for inducing stem cell differentiation consisting of the antibody and a culture medium for stem cells comprising the same.

Another object of the present invention is to provide a composition for inducing stem cell differentiation essentially consisting of the antibody and a culture medium for stem cells comprising the same.

Another object of the present invention is to provide a use of the antibody or fragment thereof for preparing a preparation for preventing or treating cancer.

Another object of the present invention is to provide a method for treating cancer comprising administering an effective amount of a composition comprising the antibody or fragment thereof as an active ingredient to a subject in need thereof.

Another object of the present invention is to provide a use of the antibody for producing a preparation for inducing stem cell differentiation.

Another object of the present invention is to provide a method for inducing stem cell differentiation comprising administering an effective amount of a composition comprising the antibody to a subject in need thereof.

Technical Solution

In order to achieve the above object, the present invention provides an agonist antibody or fragment thereof that specifically binds to a human-derived c-Met protein comprising an antibody light chain variable region (VL) comprising a complementarity determining region (CDR) L1 containing the amino acid sequence defined by SEQ ID NO: 1, a complementarity determining region (CDR) L2 containing the amino acid sequence defined by SEQ ID NO: 2 and a complementarity determining region (CDR) L3 containing the amino acid sequence defined by SEQ ID NO: 3, and an antibody heavy chain variable region (VH) comprising a complementarity determining region (CDR) H1 containing the amino acid sequence defined by SEQ ID NO: 4, a complementarity determining region (CDR) H2 containing the amino acid sequence defined by SEQ ID NO: 5 and a complementarity determining region (CDR) H3 containing the amino acid sequence defined by SEQ ID NO: 6.

In order to achieve another object of the present invention, the present invention is to provide a polynucleotide encoding the antibody or fragment thereof.

In order to achieve another object of the present invention, the present invention provides a vector comprising the polynucleotide.

In order to achieve another object of the present invention, the present invention provides a cell transformed with the vector.

In order to achieve another object of the present invention, the present invention provides a method for producing an agonist antibody or fragment thereof for binding to human c-Met, the method comprising culturing the cell under conditions in which the polynucleotide is expressed to produce a polypeptide comprising a light chain variable region and a heavy chain variable region, and recovering the polypeptide from the cell or a culture medium in which the same is cultured.

In order to achieve another object of the present invention, the present invention provides a c-Met-specific detection method comprising contacting the antibody or fragment thereof with a sample, and detecting the agonist antibody or fragment thereof.

In order to achieve another object of the present invention, the present invention provides a pharmaceutical composition for preventing or treating cancer comprising the antibody or fragment thereof as an active ingredient.

In addition, the present invention provides a pharmaceutical composition for preventing or treating cancer consisting of the antibody or fragment thereof.

In addition, the present invention provides a pharmaceutical composition for preventing or treating cancer essentially consisting of the antibody or fragment thereof.

In order to achieve another object of the present invention, the present invention provides a composition for inducing stem cell differentiation comprising the antibody.

In addition, the present invention provides a composition for inducing stem cell differentiation consisting of the antibody.

In addition, the present invention provides a composition for inducing stem cell differentiation essentially consisting of the antibody.

In order to achieve another object of the present invention, the present invention provides a culture medium for stem cells comprising the composition.

In addition, the present invention provides a culture medium for stem cells consisting of the composition.

In addition, the present invention provides a culture medium for stem cells essentially consisting of the composition.

In order to achieve another object of the present invention, the present invention provides the use of the antibody or fragment thereof for preparing a preparation for preventing or treating cancer.

In order to achieve another object of the present invention, the present invention provides a method for treating cancer comprising the antibody or fragment thereof of as an active ingredient to a subject in need thereof.

In order to achieve another object of the present invention, the present invention provides the use of the antibody for producing a preparation for inducing stem cell differentiation.

In order to achieve another object of the present invention, the present invention provides A method for inducing stem cell differentiation comprising administering an effective amount of a composition comprising the antibody to a subject in need thereof.

Hereinafter, the present invention will be described in detail.

The present invention provides an agonist antibody or fragment thereof that specifically binds to a human-derived c-Met protein comprising an antibody light chain variable region (VL) comprising a complementarity determining region (CDR) L1 containing the amino acid sequence defined by SEQ ID NO: 1, a complementarity determining region (CDR) L2 containing the amino acid sequence defined by SEQ ID NO: 2 and a complementarity determining region (CDR) L3 containing the amino acid sequence defined by SEQ ID NO: 3, and an antibody heavy chain variable region (VH) comprising a complementarity determining region (CDR) H1 containing the amino acid sequence defined by SEQ ID NO: 4, a complementarity determining region (CDR) H2 containing the amino acid sequence defined by SEQ ID NO: 5 and a complementarity determining region (CDR) H3 containing the amino acid sequence defined by SEQ ID NO: 6.

The 'c-Met protein' of the present invention is a receptor for hepatocyte growth factor (HGF), HGF is a type of cytokine that binds to the extracellular site of the c-Met receptor tyrosine kinase and induces division, movement, morphogenesis, and angiogenesis in various normal and tumor cells. c-Met is a representative receptor tyrosine kinase that exists on the cell surface, and is itself a cancer-causing gene, and sometimes, regardless of the ligand HGF, it is a protein that is involved in various mechanisms related to tumors such as cancer development, cancer metastasis, cancer cell migration, cancer cell invasion, and angiogenesis. The protein may be a polypeptide encoded by a nucleotide sequence (mRNA) represented by SEQ ID NO: 7 (NCBI Reference Sequence: NM_001127500.2), or comprises an extracellular domain thereof, and may be a polypeptide having an amino acid sequence defined by SEQ ID NO: 8 (NCBI Reference Sequence: NP_001120972).

The 'antibody', 'anti-c-Met antibody', 'humanized anti-c-Met antibody', and 'modified humanized anti-c-Met antibody' and 'anti-c-Met antibody' of the present invention is used in the broadest sense in the present invention, Specifically, it comprises monoclonal antibodies (including monoclonal antibodies, full-length monoclonal antibodies), polyclonal antibodies (polyclonal antibodies), multi-specific antibodies (e.g., bi-specific antibodies), and antibody fragments (e.g., variable regions and other portions of an antibody exhibiting a desired biological activity (e.g., binding to c-Met).

The antibody of the present invention is an antibody in which a specific amino acid sequence is included in the light and heavy chain CDRs so that it can selectively bind with c-Met, and includes both monoclonal antibodies and polyclonal antibodies, Preferably, it may be a monoclonal antibody. In addition, the antibody of the present invention includes all of a chimeric antibody, a humanized antibody, and a human antibody, and may preferably be a human antibody.

Monoclonal antibodies of the invention represent antibodies obtained from a population of substantially homogeneous antibodies, i.e., the individual antibodies constituting the population are identical except for possible naturally occurring mutations that may be present in small amounts. Monoclonal antibodies bind very specifically to a single antigenic epitope.

In the present invention, the term 'monoclonal' refers to the characteristics of the antibody and that the antibody is obtained from a substantially homologous group, it does not necessarily mean that the antibody must be produced by a specific method. For example, the monoclonal antibody of the present invention can be prepared by the hybridoma method first described in Kohler et al. (1975) Nature 256: 495, or the recombinant DNA method (see U.S. Pat. No. 4,816,567). It can also be isolated from phage antibody libraries, for example, using techniques known in the art.

The antibodies of the present invention specifically include chimeric antibodies, in which case some of the heavy and/or light chains originate from a specific species or are identical or homologous to the corresponding sequence of a specific antibody, but the remainder may be of origin from other species or identical or homologous to the corresponding sequences of other antibodies, as long as the antibody of the present invention exhibits a desirable biological activity (e.g., selective binding with NRS) (U.S. Pat. No. 4,816,567).

Humanized antibodies are antibodies that contain both human and non-human (e.g., murine, rat) antibody sequences, and in general, the rest except for the epitope-binding site (CDR) are those of human antibodies, the region that binds the epitope (CDR) may comprise a sequence of non-human origin. Complete human antibody refers to an antibody containing only the human immunoglobulin protein sequence, it can be produced in a mouse, a mouse cell, or a hybridoma originating from a mouse cell, or can be produced by a phage display method.

Natural antibodies produced in vivo are typically heterotetrameric glycoproteins of about 150,000 Daltons, consisting of two identical light chains (L) and two identical heavy chains (H). Each light chain is linked to the heavy chain by one covalent disulfide bond, but the number of disulfide chains varies between heavy chains of different immunoglobulin isotypes. Each heavy and light chain also has regularly spaced intra-chain disulfide bridges. Each heavy chain has a variable domain (VH) at one end followed by a number of constant domains. Each light chain has a variable domain (VL) at one end and a constant domain at its other end; The constant domain of the light chain is aligned with the first constant domain of the heavy chain, and the light chain variable domain is aligned with the variable domain of the heavy chain. It is believed that special amino acid residues form an interface between the light chain variable domain and the heavy chain variable domain. The "variable region" or "variable domain" of an antibody refers to the amino-terminal domain of the heavy or light chain of an antibody. The variable region of the heavy chain is described as "VH", and the variable region of the light chain is described as "VL". These domains are generally the most variable portions of an antibody and contain an antigen binding site.

In the present invention, 'hypervariable' means that several sequences within the variable region are widely different in sequence between antibodies, it refers to the fact that it contains residues that are directly related to the binding and specificity of each particular antibody for its specific antigenic determinants. Hypervariability in both the light and heavy chain variable regions is concentrated in three segments known as complementarity determining regions (CDR) or hypervariable loops (HVL). CDRs are defined by sequence comparison in Kabat et al., 1991, In: Sequences of Proteins of Immunological Interest, 5th Ed. Public Health Service, National Institutes of Health, Bethesda, MD., whereas HVL is structurally defined according to the three-dimensional structure of the variable region, as disclosed in the literature (Chothia. and Le Na 1987, J. Mol. Biol. 196:901-917).

The three CDRs in each of the heavy and light chains are separated by a frame region (FR), which contains sequences that tend to be less variable. From the amino terminus to the carboxy terminus of the heavy and light chain variable regions, the FRs and CDRs are arranged in the following order: FR1, CDR1, FR2, CDR2, FR3, CDR3 and FR4. The large β sheet arrangement of the FR brings the CDRs inside each of the chains closer to each other as well as to the CDRs from other chains. The resulting form contributes to the antigen binding site, but not all CDR residues need to be directly involved in antigen binding.

The fragment of the present invention is characterized in that it is a fragment selected from the group consisting of diabody, Fab, Fab', F(ab)2, F(ab')2, Fv and scFv.

In the present invention, an antibody fragment refers to a fragment of an antibody that maintains the antigen-specific binding ability of the entire antibody, and preferably the fragment retains at least 20%, 50%, 70%, 80%, 90%, 95% or 100% or more of the affinity of the human-derived c-Met protein of the parent antibody. Specifically, it may be in the form of Fab, F(ab)2, Fab', F(ab')2, Fv, diabody, scFv, and the like.

Fab (fragment antigen-binding) is an antigen-binding fragment of an antibody, and consists of one variable domain and a constant domain of each of the heavy and light chains. F(ab')2 is a fragment produced by hydrolyzing an antibody with pepsin, two Fabs are linked by a disulfide bond at a heavy chain hinge. F(ab') is a monomeric antibody fragment in which a heavy chain hinge is added to a Fab separated by reducing the disulfide bond of the F(ab')2 fragment. variable fragment (Fv) is an antibody fragment consisting only of the variable regions of each of the heavy and light chains. A single chain variable fragment (scFv) is a recombinant antibody fragment in which a heavy chain variable region (VH) and a light chain variable region (VL) are connected by a flexible peptide linker. Diabody refers to a fragment in which the VH and VL of the scFv are connected by a very short linker and cannot be bonded to each other, and the VL and VH of the other scFv of the same form are each bonded to form a dimer.

For the purposes of the present invention, the antibody fragment is not limited in structure or form as long as it maintains the binding specificity to human-derived c-Met protein, but may preferably be scFv. The scFv according to the present invention has a CDR composition specific to the human-derived c-Met protein, or a composition of VH and VL, and the sequence is not particularly limited, if the C-terminus of VH and the N-terminus of VL are connected through a linker, The type of the linker is not particularly limited as long as it is known in the art as a linker applied to scFv.

The antibody or fragment thereof of the present invention may contain conservative amino acid substitutions (referred to as conservative variants of the antibody) that do not substantially alter their biological activity.

In addition, the antibody or fragment thereof of the present invention described above may be conjugated to an enzyme, a fluorescent substance, a radioactive substance, and a protein, but is not limited thereto. In addition, methods for conjugating the substance to an antibody are well known in the art.

The antibody of the present invention may be derived from any animal including mammals, birds, and the like, including humans. Preferably, the antibody may be an antibody of human, mouse, donkey, sheep, rabbit, goat, guinea pig, camel, horse, or chicken, most preferably human or mouse.

Human antibodies are antibodies having the amino acid sequence of human immunoglobulins, transfected against antibodies isolated from human immunoglobulin libraries or one or more human immunoglobulins, and Intrinsic immunoglobulins include antibodies isolated from animals that do not express (see U.S. Pat. No. 5,939,598).

The antibody of the present invention may be conjugated to an enzyme, a fluorescent material, a radioactive material, a protein, etc., but is not limited thereto. In addition, methods for conjugating the substance to an antibody are well known in the art.

The present invention provides a polynucleotide encoding the antibody or fragment thereof.

In the present invention, 'polynucleotide' may be described as an oligonucleotide or a nucleic acid, and the analogs of the DNA or RNA (e.g., peptide nucleic acids and non-naturally occurring nucleotide analogs) and hybrids thereof generated using DNA molecules (e.g., cDNA or genomic DNA), RNA molecules (e.g., mRNA), and nucleotide analogs are included. The polynucleotide may be single-stranded or double-stranded. The polynucleotide refers to a nucleotide sequence encoding an antibody composed of heavy and light chains having a CDR configuration or a configuration of VH and VL specific to the KRS N-terminal region described above.

The polynucleotide of the present invention is not particularly limited in its sequence as long as it encodes the antibody or fragment thereof of the present invention. The polynucleotide encoding the CDR sequence described above in the antibody according to the present invention described above is not particularly limited in its sequence, but preferably, it may include the nucleotide sequence defined by SEQ ID NO: 1 (heavy chain CDR1), SEQ ID NO: 2 (heavy chain CDR2), SEQ ID NO: 3 (heavy chain CDR3), SEQ ID NO: 4 (light chain CDR1), SEQ ID NO: 5 (light chain CDR2), and SEQ ID NO: 6 (light chain CDR3). In addition, the sequence of the polynucleotide encoding the VH and VL described above in the antibody according to the present invention is not particularly limited.

The polynucleotide encoding the antibody or fragment thereof of the present invention can be obtained by a method well known in the art. For example, based on a DNA sequence encoding a part or all of the heavy and light chains of the antibody or the corresponding amino acid sequence, it can be synthesized using an oligonucleotide synthesis technique well known in the art, for example, a polymerase chain reaction (PCR) method.

The present invention provides a vector comprising the polynucleotide.

The 'vector' of the present invention is used for the purpose of replication or expression of the polynucleotide of the present invention for recombinant production of the antibody or fragment thereof of the present invention. It generally comprises one or more of a signal sequence, an origin of replication, one or more marker genes, an enhancer element, a promoter, and a transcription termination sequence. The vector of the present invention may preferably be an expression vector, more preferably a vector comprising a polynucleotide of the present invention operably linked to a regulatory sequence, for example, a promoter.

A plasmid, a type of vector, refers to a linear or circular double helix DNA molecule to which external polynucleotide fragments can be bound. Another form of vector is a viral vector (e.g., replication defective retroviruses, adenoviruses and adeno-associated viruses), and here, additional DNA fragments may be introduced into the viral genome. Certain vectors are capable of autonomous replication within the host cell (bacterial vectors, including, for example, bacterial origin and episomal mammalian vectors) into which they are introduced. Other vectors (e.g., non-episomal mammalian vectors) are integrated into the genome of the host cell by introduction into the host cell, and thereby replicated together with the host genome.

In the present invention, the 'expression vector' is a form of a vector capable of expressing a selected polynucleotide. A polynucleotide sequence is "operably linked" to the regulatory sequence when the regulatory sequence affects the expression (e.g., level, timing or location of expression) of the polynucleotide sequence. The regulatory sequence is a sequence that affects the expression (e.g., level, timing or location of expression) of the nucleic acid to which it is operably linked. The regulatory sequence may, for example, have its effect on the regulated nucleic acid, either directly or through the action of one or more other molecules (e.g., polypeptides that bind to the regulatory sequence and/or the nucleic acid). The regulatory sequences include promoters, enhancers and other expression control elements. The vector of the present invention may preferably be pOptiVEC™-TOPO and pcDNA™3.3-TOPO.

The present invention provides cells transformed with the vector.

The type of the cell of the present invention is not particularly limited as long as it can be used to express the polynucleotide encoding the antibody or fragment thereof contained in the expression vector of the present invention.

Cells (host cells) transformed with the expression vector according to the present invention may be included prokaryotes (e.g., *E. coli*), eukaryotes (e.g., yeast or other fungi), plant cells (e.g., tobacco or tomato plants cells), animal cells (e.g., human cells, monkey cells, hamster cells, rat cells), mouse cells, insect cells, or hybridomas derived from them. Preferably, it may be a cell derived from mammals including humans.

Prokaryotes suitable for this purpose include gram-negative or gram-positive organisms, for example Enterobacteriaceae, for example *Escherichia*, for example *E. coli*, *Enterobacter, Erwinia, Klebsiella, Proteus, Salmonella*, for example *Salmonella typhimurium, Serratia*, for example *Serratia marcescans* and *Shigella*, and Bacilli, for example *B. subtilis* and *B. licheniformis, Pseudomonas*, for example *P. aeruginosa* and *Streptomyces*. The cell of the present invention is not particularly limited as long as it is capable of expressing the vector of the present invention, preferably it may be *E. coli*.

As the cell of the present invention, *Saccharomyces cerevisiae* is most commonly used in eukaryotes. However, many other genera, species and strains, but not limited thereto, for example, *Schizosaccharomyces pombe, Kluyveromyces* host, for example *K. lactis, K. fragilis* (ATCC 12,424), *K. Bulgaricus* (ATCC 16,045), *K. Wickeramii* (ATCC 24,178), *K. waltii* (ATCC 56,500), *K. Drosophilarum* (ATCC 36,906), *K. Thermotolerans* and *K. marxianus; yarrowia* (EP 402,226); *Pichia pastoris* (EP 183,070);

*Candida; Trichoderma* reesia (EP 244,234); *Neurospora crassa; Schwanniomyces*, for example *Schwanniomyces occidentalis*; and filamentous fungi, for example *Neurospora, Penicillium, Tolypocladium* and *Aspergillus* hosts, for example *A. nidulans* and *A. niger* can be used.

The term 'transformation' refers to a modification of the genotype of a host cell by introducing an exogenous polynucleotide, and it means that the foreign polynucleotide has been introduced into the host cell, irrespective of the method used for the transformation. The foreign polynucleotide introduced into the host cell may be integrated and maintained or unintegrated and maintained into the genome of the host cell, the present invention includes both.

The recombinant expression vector capable of expressing the antibody or fragment thereof that specifically binds to the human-derived c-Met protein according to the present invention can be transformed introducing into a cell for producing an antibody or fragment thereof by a method known in the art, for example, but is not limited thereto, transient transfection, microinjection, transduction, cell fusion, calcium phosphate precipitation, liposome-mediated transfection, polybrene-mediated transfection, electroporation, gene gun, and known methods for introducing nucleic acids into cells.

In addition, the cells of the present invention are cultured cells that can be transformed or transfected with the polynucleotide or a vector containing the same of the present invention, and it can continue to be expressed in the host cell. Recombinant cells refer to cells transformed or transfected with a polynucleotide to be expressed. The cells of the invention also contain the polynucleotides of the invention, unless a regulatory sequence is introduced into the cell such that it is operably linked to the polynucleotide, it may be a cell that does not express the desired level.

The cells of the present invention can be cultured in a variety of media. Commercially available media such as Ham's F10 (Sigma-Aldrich Co., St. Louis, MO), minimal essential media (MEM, Sigma-Aldrich Co.), RPMI-1640 (Sigma-Aldrich Co.), and Dulbecco's modified Eagle's medium (DMEM, Sigma-Aldrich Co.) is suitable for culturing cells. Hormones and/or other growth factors, salts, buffers, nucleotides, antibiotics, trace elements and glucose or equivalent energy sources may be added to the medium, if necessary.

The present invention provides a method for producing an agonist antibody or fragment thereof that binds to human c-Met, the method comprising culturing the cell under conditions in which the polynucleotide is expressed to produce a polypeptide comprising a light chain variable region and a heavy chain variable region, and recovering the polypeptide from the cell or a culture medium in which the same is cultured.

The cell of the production method in the present invention is as described above, and it contains a polynucleotide encoding the antibody of the present invention. The polypeptide of the production method may be an antibody of the present invention or a fragment thereof, and other amino acid sequences other than the antibody or fragment thereof of the present invention may be additionally bound. In this case, it can be removed from the antibody or fragment thereof of the present invention using a method well known to those skilled in the art. The culture medium composition and culture conditions may vary depending on the type of cells, which can be appropriately selected and adjusted by a person skilled in the art.

The antibody molecule accumulates in the cytoplasm of the cell, or is secreted from the cell, or can be targeted to periplasm or extracellular medium (supernatant) by an appropriate signal sequence, it is preferred to be targeted with periplasm or extracellular medium. In addition, it is preferable to refold the produced antibody molecule using a method well known to those skilled in the art and to have a functional conformation. The recovery of the polypeptide may vary depending on the characteristics of the produced polypeptide and the characteristics of the cell, which can be appropriately selected and adjusted by those of ordinary skill in the art.

The polypeptide may be produced intracellularly, in the surrounding cytoplasmic space, or may be directly secreted into the medium. If the polypeptide is produced inside the cell, the cell can be destroyed to release the protein as a first step. Particulate debris, host cells or lysed fragments are removed, for example by centrifugation or ultrafiltration. When the antibody is secreted into the medium, the supernatant from this expression system is generally first concentrated using a commercially available protein concentration filter, such as an Amicon or Millipore Pellicon ultrafiltration unit. Protease inhibitors such as PMSF can be included in any preceding step to inhibit proteolysis, and antibiotics may be included to prevent the growth of accidental contaminants.

Antibodies prepared from cells can be purified using, for example, hydroxyapatite chromatography, gel electrophoresis, dialysis and affinity chromatography, the antibody of the present invention can be preferably purified through affinity chromatography.

The present invention provides a c-Met-specific detection method comprising contacting the antibody or fragment thereof with a sample and detecting the agonist antibody or fragment thereof.

The detection method of the present invention may comprise the steps ((1) Step) of preparing a sample for measuring the presence and concentration of KRS (or KRS N-terminal peptide exposed to the extracellular membrane) using the antibody or fragment thereof according to the present invention before contacting the antibody or fragment thereof according to the present invention with a sample.

A person skilled in the art can appropriately select a known method for detecting a protein using an antibody, and prepare a sample suitable for the selected method. In addition, the sample may be cells or tissues, blood, whole blood, serum, plasma, saliva, cerebrospinal fluid, etc. obtained by a biopsy or the like collected from a subject to be diagnosed with cancer or cancer metastasis. The method of detecting a protein using the antibody is not limited thereto, but for example, Western blot, immunoblot, dot blot, immunohistochemistry, enzyme immunoassay (ELISA), radioimmunoassay, competitive binding assay, and immunoprecipitation etc. For example, in order to perform western blot, it can be prepared by adding a buffer suitable for electrophoresis to a sample or cell lysate and boiling it, and pre-treatment such as fixing and blocking sections of cells or tissues can be performed for immunohistochemical staining.

Next, a step (step (2)) of contacting the antibody or fragment thereof according to the present invention with the sample prepared in the above step is performed.

The antibody according to the present invention is an antibody or fragment thereof that has the above-described CDR or VH and VL configuration and specifically binds to a human c-Met protein, and its specific type and sequence configuration are as described above.

The antibody or fragment thereof may be labeled with a generally detectable moiety for its 'detection'. For example, it can be labeled with radioactive isotopes or fluorescent labels using techniques known in the art. Alternatively, various enzyme-substrate labels may be used, and examples of the enzymatic label include luciferase such as *Drosophila* luciferase and bacterial luciferase (U.S. Pat. No. 4,737,456), luciferin, 2,3-dihydrophthalagindiones, maleate dehydrogenase, urase, peroxidase such as horseradish peroxidase (HRPO), alkaline phosphatase, β-galactosidase, glucoamylase, lysozyme, saccharide oxydases (e.g., glucose oxidase, galactose oxidase, and glucose-6-phosphate dehydrogenase), heterocyclic oxidases (e.g., uricase and xanthine oxidase), lactoferoxidase, microperoxy etc. Techniques for conjugating enzymes to antibodies are known in the art. Labels can be conjugated directly or indirectly to the antibody using a variety of known techniques. For example, an antibody can be conjugated to biotin and any of the labels belonging to the three broad categories mentioned above can be conjugated with avidin, or vice versa. Biotin binds selectively to avidin, so this label can be conjugated to the antibody in this indirect manner.

Alternatively, to achieve indirect conjugation of the label to the antibody, the antibody can be conjugated with a small hapten (e.g., digoxin) and one of the different types of labels mentioned above can be conjugated to an anti-hapten antibody (e.g., an anti-dioxin antibody). Thus, indirect conjugation of the label to the antibody can be achieved.

In the present invention, the term 'contacting' is used in its general meaning, and means mixing, bonding, or bringing two or more substances into contact with each other. The contacting may be performed in vitro or in other containers, and may also be performed in situ, in vivo, in an individual, in a tissue, or in a cell.

Next, a step (step (3)) of detecting the antibody or fragment thereof according to the present invention in the sample after step (2) is performed.

The 'detection' targets the antibody or fragment thereof and a complex of an antigen according to the present invention formed in a sample, it means detecting the presence or absence of a human c-Met peptide (or a protein containing the same) or measuring the level of the peptide (including both qualitative or quantitative measurements). Therefore, after performing the step (2) and before the detection step (step (3)) described later, a step of removing excess antibodies or fragments thereof that do not form a complex with the human c-Met protein may be further included.

When the antibody or fragment thereof used in step (2) above contains a detectable moiety such as directly labeled with fluorescence, radioisotope, enzyme, the detection can be performed according to a method known in the art for detecting the moiety. For example, radioactivity may be measured by, for example, scintillation counting, and fluorescence may be quantified using a fluorimeter.

In addition, when the antibody or fragment thereof used in step (2) does not itself contain the aforementioned detection moiety, as known in the art, it can be detected indirectly using a secondary antibody labeled with fluorescence, radioactivity, enzyme, or the like. The secondary antibody binds to the antibody or fragment thereof (primary antibody) according to the present invention.

Through recent studies, HGF/SF also acts on the nervous system, and in particular, many studies have been reported on the protective function of motor neurons (Novak et al., Journal of Neuroscience. 20:326-337, 2000). In addition, it has been suggested that it plays an important function in the defensive physiological mechanisms following general organ damage such as heart damage recovery (Nakamura et al., J Clin Invest. 106:1511-1519, 2000), in fact, the HGF/MET pathway is involved in the process of nerve infarction, progressive nephritis, cirrhosis and pulmonary fibrosis, and it has been demonstrated that HGF is overexpressed in the lesions of these degenerative diseases and thus exhibits protective activity as a physiological defense mechanism for tissue damage (Comoglio et al., Nature Review Drug Discovery. 7:504-516, 2008). In addition, the hyperactivity of HGF/c-Met signaling is related to malignant tumor formation and angiogenesis of various endothelial cells, from this point of view, it was suggested that an antagonistic c-Met antibody targeting c-Met could be used as an anticancer agent (Comoglio et al., Nature Review Drug Discovery. 7:504-516, 2008). For example, it has been reported that a c-Met antibody having one branch negatively regulates the activation of HGF by c-Met dimerization, thereby effectively inhibiting tumor growth in a transplant mouse model (Jin et al, Cancer Research 68 (11): 4360-4368, 2008; Comoglio et al., Nature Review Drug Discovery. 7:504-516, 2008). In addition, in T-cell genetic engineering that selectively recognizes cancer cell surface antigens in T-cell therapy, antibodies against antigens that are overexpressed in cancer cells are being used for tumor targeting for T-cell linkage (Sadelain, The Cancer Journal 15 (6): 451-455, 2009).

The present invention provides a pharmaceutical composition for preventing or treating cancer comprising the antibody or fragment thereof as an active ingredient.

The antibodies and fragments thereof according to the present invention have excellent specific binding ability to the c-Met protein, and the c-Met antibody or fragment thereof negatively regulates the activation of HGF to inhibit tumor growth, and thus can be used as a cancer therapeutic agent. In addition, it can be used for preventing or treating cancer by binding a cancer therapeutic agent to the antibody or fragment thereof, and the antibody or fragment can be prepared in a suitable form together with a pharmaceutically acceptable carrier and used for cancer prevention or treatment.

The 'cancer' of the present invention is not limited thereto, but may include bladder cancer and breast cancer, cervical cancer, cholangiocarcinoma, colorectal cancer, colon cancer, endometrial cancer, esophageal cancer, gastric cancer, head and neck cancer, kidney cancer, liver cancer, lung cancer, nasopharyngeal cancer, ovarian cancer, pancreatic cancer, gallbladder cancer, prostate cancer, thyroid cancer, osteosarcoma, rhabdomyosarcoma, synovial sarcoma, Kaposi's sarcoma, leiomyosarcoma, malignant fibrous histiocytoma, fibrosarcoma, acute myelogenous leukemia, adult T cell leukemia, chronic myelogenous leukemia, lymphoma, multiple myeloma, glioblastoma, astrocytoma, melanoma, mesothelioma, Wilm's tumor, and clear cell sarcoma (CCS), acinar soft sarcoma (ASPS), and MiT tumors including translocation-associated renal cell carcinoma.

The pharmaceutical composition according to the present invention contains the agonist antibody or fragment thereof that specifically binds to the c-Met protein, or it can be formulated in a suitable form with a pharmaceutically acceptable carrier, and it may further contain excipients or diluents. In the above, 'pharmaceutically acceptable' is physiologically acceptable and when administered to humans, it generally refers to a non-toxic composition that does not cause allergic reactions or similar reactions such as gastrointestinal disorders, dizziness, and the like.

The pharmaceutically acceptable carrier may further include, for example, a carrier for oral administration or a carrier for parenteral administration. Carriers for oral administration may include lactose, starch, cellulose derivatives, magnesium stearate, stearic acid, and the like. In addition, it may contain various drug delivery substances used for oral administration of the peptide preparation. In addition, the carrier for parenteral administration may include water, suitable oils, saline, aqueous glucose and glycol, and the like, and may further include stabilizers and preservatives. Suitable stabilizers are antioxidants such as sodium hydrogen sulfite, sodium sulfite or ascorbic acid. Suitable preservatives are benzalkonium chloride, methyl- or propyl-paraben and chlorobutanol. The pharmaceutical composition of the present invention may further include a lubricant, a wetting agent, a sweetening agent, a flavoring agent, an emulsifying agent, a suspending agent, and the like in addition to the above components. Other pharmaceutically acceptable carriers and preparations may be referred to those known in the art.

The composition of the present invention can be administered to mammals including humans by any method. For example, it can be administered orally or parenterally. The parenteral administration method may be intravenous, intramuscular, intraarterial, intramedullary, intrathecal, intracardiac, transdermal, subcutaneous, intraperitoneal, intranasal, intestinal, topical, sublingual or rectal administration, but it not limited thereto.

The pharmaceutical composition of the present invention can be formulated as a formulation for oral administration or parenteral administration according to the route of administration as described above.

In the case of a formulation for oral administration, the composition of the present invention may be formulated using a method known in the art as a powder, granule, tablet, pill, dragee, capsule, liquid, gel, syrup, slurry, suspension, etc. For example, in oral preparations, tablets or dragees can be obtained by blending the active ingredient with a solid excipient, pulverizing it, adding a suitable auxiliary, and processing into a granule mixture. Examples of suitable excipients may be included sugars including lactose, dextrose, sucrose, sorbitol, mannitol, xylitol, erythritol and maltitol, and starches including corn starch, wheat starch, rice starch and potato starch, cellulose including cellulose, methyl cellulose, sodium carboxymethylcellulose, hydroxypropylmethyl-cellulose, and the like, fillers such as gelatin, polyvinylpyrrolidone, and the like. In addition, in some cases, cross-linked polyvinylpyrrolidone, agar, alginic acid or sodium alginate may be added as a disintegrant. Furthermore, the pharmaceutical composition of the present invention may further include an anti-aggregating agent, a lubricant, a wetting agent, a flavoring agent, an emulsifying agent and a preservative and the like.

In the case of a formulation for parenteral administration, it can be formulated in the form of injections, creams, lotions, ointments for external use, oils, moisturizers, gels, aerosols, and nasal inhalants by methods known in the art. These formulations are described in formulas generally known to all pharmaceutical chemistry.

The total effective amount of the composition of the present invention may be administered to a patient in a single dose, It can be administered by a fractionated treatment protocol that is administered for a long period of time in multiple doses. The pharmaceutical composition of the present invention may vary the content of the active ingredient according to the severity of the disease. Preferably, the preferred total dose of the pharmaceutical composition of the present invention may be about 0.01 µg to 10,000 mg, most preferably 0.1 µg to 500 mg per 1 kg of the patient's body weight per day.

However, the dosage of the pharmaceutical composition is determined by considering various factors such as the age, weight, health status, sex, severity of the disease, diet and excretion rate of the patient, as well as the formulation method, route of administration and number of treatments. Therefore, considering these points, one of ordinary skill in the art will be able to determine an appropriate effective dosage of the composition of the present invention. The pharmaceutical composition according to the present invention is not particularly limited in its formulation, route of administration, and method of administration as long as it exhibits the effects of the present invention.

The present invention provides a composition for inducing stem cell differentiation comprising the antibody.

The 'stem cells' of the present invention collectively refer to undifferentiated cells having stemness capable of differentiating into various cells, stem cells are differentiated into specific cells by specific differentiation factors and/or environments. Types of stem cells include embryonic stem cells, embryonic germ cells, adult stem cells, and cancer stem cells.

Stem cells can be used to treat various diseases including regeneration of damaged tissue, diabetes, leukemia, Parkinson's disease, heart disease, spinal cord trauma, etc. most preferably, it may be a fat-derived mesenchymal stem cell in the present invention.

The present invention provides a culture medium for stem cells comprising the composition for inducing stem cell differentiation.

'The culture medium for stem cells' of the present invention is a medium containing a composition for inducing stem cell differentiation containing the c-Met antibody, and is a medium containing a component for culturing or differentiating stem cells. The medium includes a medium capable of differentiating stem cells into all cells such as fat, cartilage, bone, and nerve, and preferably, may be a medium for differentiating stem cells into adipocytes, chondrocytes, or cartilage cells.

In one embodiment of the present invention, a sample with increased output was obtained by screening a human scFv library using a human recombinant c-Met antibody, then by checking the binding force through the ELISA method, a sample showing a binding signal was selected and subjected to nucleotide sequence analysis. Then, hits having different sequences were selected and the binding force was checked by ELISA, and the ten most strongly bound hits were selected and converted into human IgG form (see Example 1, FIGS. 1a, 1b, and 2).

In another embodiment of the present invention, in order to confirm that human IgG binds to natural c-Met, after transfecting 293F cells with a plasmid, cells were obtained, and the antibody was purified with protein A beads, followed by SDS-PAGE, it was confirmed that the above 10 hits were converted into human IgG form and expressed in cells, and the sizes of the light and heavy chains were confirmed. Then, as a result of flow cytometric analysis using c-Met positive cells, four antibodies having the highest change in the binding pattern of the antibody and the expression level of c-Met matched in cells were selected (see Example 2, FIGS. 3, 4a and 4b).

In another embodiment of the present invention, the human c-Met recombinant protein, which is an antigen, was immobilized on a biosurface, and then antibodies (A8, A11, and C8) were flowed to react with the antigen, and the binding site was measured.

As a result of performing the analysis on the Octat platform, it was confirmed that all three antibodies had high affinity and dissociation values compared to the existing c-Met antibodies (see Example 3 and FIG. 5).

In another embodiment of the present invention, after culturing a cell line positive for c-Met to obtain a protein, as a result of confirming the c-Met signal pattern by the Western blot method, it was confirmed that phosphorylation of the c-Met catalyst did not occur only in the H596 cell line. Then, as a result of Western blot treatment after treatment with HGF at different concentrations of H596 cells, it was confirmed that the expression levels of Tyr1234 and Tyr1349 were increased in a concentration-dependent manner. Then, as a result, H596 cells were treated with HGF and c-Met antibodies A8, A11, B10, C8 by concentration, and Western blot was performed, it was confirmed that HGF, A8, and A11 induce phosphorylation signals including major downstream signals such as p-Erk and p-Akt (see Example 4 and FIGS. 6a to 6c).

In another embodiment of the present invention, as a result of analyzing cell proliferation by the WST assay method by varying the concentration of HGF, A8 or A11 in H596 cells, although the antibody-treated case did not show the same cell proliferation rate as the HGF-treated case, it was confirmed that the saturation point was higher (see Example 5 and FIG. 7).

In another embodiment of the present invention, mesenchymal stem cells were cultured using a medium without HGF, a medium containing different concentrations of HGF, A8 or A11, as a result of observing incubation time, viability and cell morphology during cultivation, it was found that the average viability of cells in all groups was 90% or more. Accordingly, it was confirmed that the c-Met antibody did not affect the culture form of stem cells (see Example 6-1, FIGS. 8a and 8b).

In another embodiment of the present invention, adipose-derived mesenchymal stem cells were cultured by treatment with HGF, A8 or A11, and then adipose, cartilage, and bone differentiation were induced. Differentiation of stem cells was induced under different medium conditions according to the cell lineage to be differentiated, as a result of staining and observing each cell, stem cells differentiated into adipocytes in all medium conditions, and cartilage and bone differentiation did not appear in the medium without HGF, it was confirmed that A8 or A11 showed similar results to HGF. Accordingly, it was confirmed that A8 or A11 played the same role as HGF in stem cells (see Example 6-2 and FIGS. 9a to 9d).

In addition, the present invention provides the use of the antibody or fragment thereof for preparing an agent for preventing or treating cancer.

In addition, the present invention provides a method for treating cancer comprising administering an effective amount of a composition comprising the antibody or fragment thereof as an active ingredient to a subject in need thereof.

The present invention provides the use of the antibody for producing a preparation for inducing stem cell differentiation.

The present invention provides a method for inducing stem cell differentiation comprising administering an effective amount of a composition comprising the antibody to a subject in need thereof.

The 'effective amount' of the present invention refers to an amount that, when administered to a subject, shows an effect of improving, treating, preventing, detecting, diagnosing, or reducing cancer, it refers to the amount showing the effect of inducing stem cell differentiation. The 'subject' may be an animal, preferably an animal including a mammal, especially a human, and may be cells, tissues, organs, etc. derived from animals. The subject may be a patient in need of the effect.

The 'treatment' of the present invention generically refers to improving the symptoms of cancer or cancer, this may include curing, substantially preventing, or improving the condition of cancer, it includes alleviating, curing or preventing one symptom or most of the symptoms resulting from cancer, but is not limited to.

In the present invention, the term 'comprising' is used in the same way as 'containing' or 'as a feature', in the composition or method, additional component elements or method steps, etc. not mentioned are not excluded. The term 'consisting of' means excluding additional elements, steps, or ingredients that are not separately described. The term 'essentially consisting of' means including, in the scope of a composition or method, a component element or step that does not substantially affect its basic properties in addition to the described component elements or steps.

Advantageous Effect

Accordingly, the present invention provides anti-c-Met agonist antibodies and uses thereof. The method of the present invention can be usefully used to detect c-Met antibody, induce stem cell differentiation using the antibody, and to treat or prevent cancer.

BRIEF DESCRIPTION OF THE DRAWINGS

FIG. 2 shows the result of confirming whether or not the selected hit is bound according to the ELISA result.

MODE FOR CARRYING OUT INVENTION

Figure 1A:
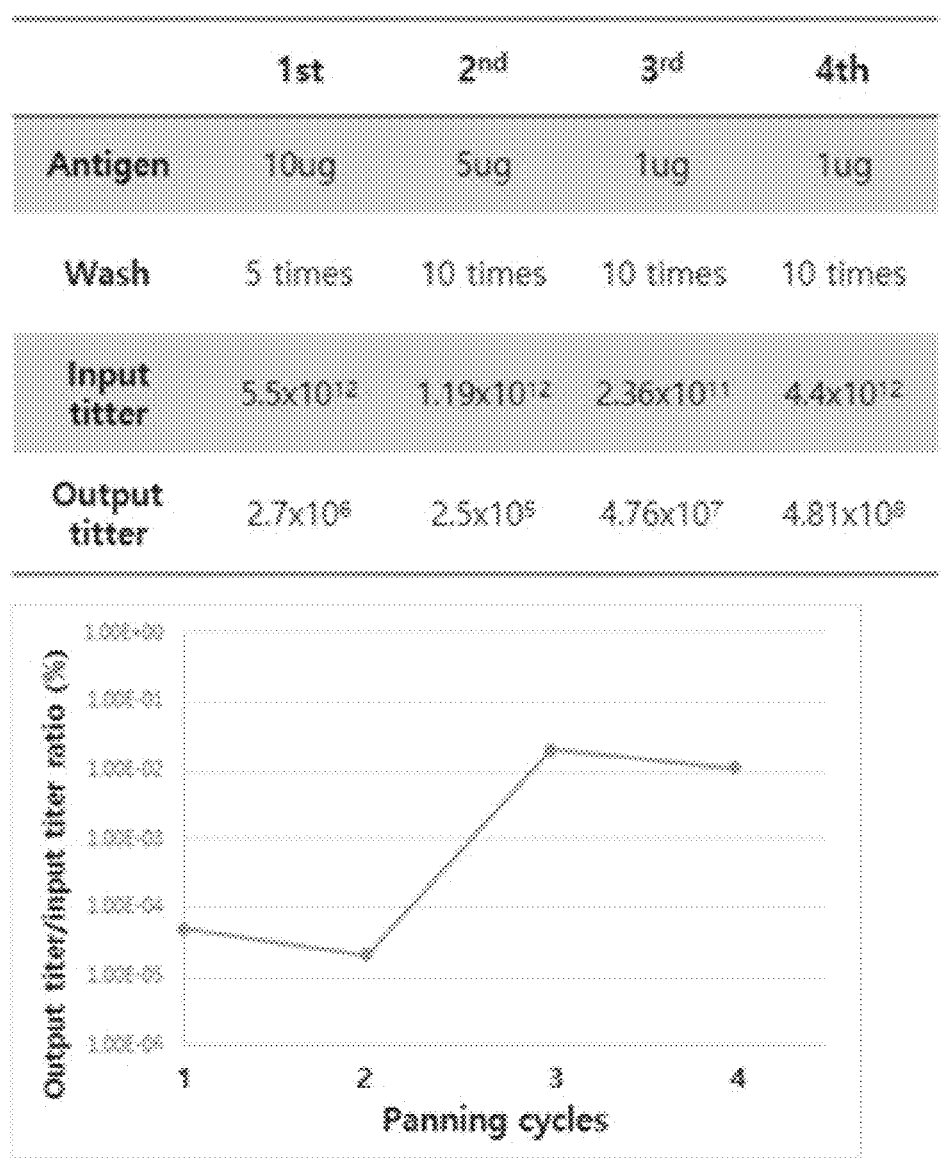
FIGS. 1a and 1b show phage display using human c-Met recombinant protein as an antigen (FIG. 1a) and results of screening by ELISA (FIG. 1b).

Hereinafter, the present invention will be described in detail.

However, the following examples are only illustrative of the present invention, and the contents of the present invention are not limited to the following examples.

Experiment Method

Reagent

A549 cell line, MDA-MB231 cell line was purchased from ATCC (American Type Culture Collection, USA), H596 cells and SKBR-3 cells were purchased from the Korean Cell Line Bank (KCLB). Adipose derived mesenchymal cells were provided by Xcell Therapeutics (Seoul). In addition, a culture medium for culturing mesenchymal stem cells was purchased from Xcell Therapeutics. The antigen used for selection was a human c-Met recombinant protein containing 1-932 amino acids (amino acid, aa) of the receptor, and was purchased from Sinobiological (China). In addition, as a control, an anti-c-Met antibody purchased from Abcam (USA) was used.

Phage Display

Human recombinant c-Met protein was used as an antigen, and the human scFv library was used for screening for hits that bind to the c-Met extracellular region. The antigen was coated on an immune tube (Nunc, USA) having a concentration of 10 μg/μl and incubated with O/N to bind. The immune tube and phage were inhibited by blocking buffer (3% milk in PBST). Phage was put into an antigen-coated immunotube and bound, and after 1 hour, it was washed 4 times with PBST and 1 time with PBS. Phage was eluted in 100 mM TEA for 7-8 minutes and then neutralized with Tris-HCl (pH 8) solution. The eluted phage was infected with E. coli, and some were cultured in O/N on a solid LA plate to check the output titer. The remaining phage was rescued using a helper phage, and the same experiment was repeated 3 times.

ELISA Screening

After the fourth panning, a single colony was injected into 150 μl of SB containing ampicillin in each 96-well plate. Then, it was cultured in a shaking incubator at 37° C. until the medium became cloudy. After incubation, the culture solution was put on a disk and induced with 1 nM IPTG, followed by incubation at 30° C. overnight. c-Met recombinant protein was used as an antigen, dissolved in PBS at a concentration of 1 μg/ml on an ELISA plate (corning 3690), coated, and incubated overnight at 4° C. The next day, the plate into which the clones were injected was centrifuged at 3000 rpm for 15 minutes. The supernatant was removed, and the pellet was resuspended in 1×TES buffer at 37° C. for 5 to 7 minutes, and then 0.2×TES buffer was added and reacted at 4° C. for 30 minutes to lyse the cells. The antigen-coated plate was washed 3 times with 150 μl of TBST, and the reaction was inhibited using 3% skim milk. A periplasmic extract was obtained from the lysed cells, and the reaction was inhibited for 1 hour using 6% skim milk in a new plate. Then, the solution was added to the antigen-coated plate, after incubation at room temperature for 1 hour, it was washed 3 times with TBST. Then, anti-HA Hrp secondary antibody was added, incubated for 1 hour, and washed 3 times with TBST. Then, 30 μl of TMB was treated to initiate the reaction, and then the reaction was inhibited using 1N $H_2SO_4$, and detected at 450 nm.

Sequence Analysis and IgG Conversion

The sequence of hits selected in the ELISA screening was analyzed (Cosmogenetech, Korea). Final hits selected after sequencing and ELISA screening were converted to human IgG. The scFv sequence was converted to human light and heavy chain sequences, and was fused to pOptiVEC™-TOPO and pcDNA™3.3-TOPO (Thermofisher, USA) vectors by cloning. Then, the plasmid was amplified using midi prep (Macherey Nagel, Germany).

Overexpression and Antibody Purification

The amplified plasmid was temporarily expressed using the Freestyle Expression System (Invitrogen, USA). Freestyle cells were thawed and cultured in Freestyle Expression Medium in an Erlenmeyer flask (Corning, USA).

Cells were cultured to a concentration of 3.0×106 cells/ml and subcultured every 2 to 3 days. After passage 4 times, heavy and light chain plasmids were transfected using FreeStyle™ MAX Transfection reagent (Invitrogen, USA). Then, the cells were cultured in a shaker under conditions of 8% CO2 and 37° C. Cells were obtained 7 days after transfection, and the supernatant was obtained and filtered. After filtration, the supernatant was applied to MabSelect SuRe protein A beads (GE healthcare. USA) in a chromatography column (Bio-rad, USA). Then, the size was confirmed by SDS-PAGE and Coomassie blue staining.

Flow Cytometry

Flow cytometric analysis was performed using A549, MDA-MP231, H596 and SKBR-3 cells. The cells were removed with a cell dissociation buffer (Hyclone, USA), washed with PBS, and then separated into 2.0×105 cells and placed in a tube. The antibody was diluted with DBPS (Wellgene) solution containing 2% FBS to a concentration of 1 μg/tube, added to cells, and reacted for 1 hour. As a control, a commercial anti-c-Met antibody was used. Then, the cells were washed twice and reacted with a secondary antibody conjugated to FITC for 40 minutes. After washing three times, it was analyzed using FACS BD Calibur (BD, USA).

Octet Analysis

Octet service was provided by PALL corp, Fortebio. His-tagged human recombinant c-Met protein (Sinobiological, China) was used as an antigen. The target was captured by 12 Ni-NTA sensors at a concentration of 20 ug/ml on the bio-surface. PBS was used as a ligand buffer, and 1 xFortebio Kinetic buffer was used as an analyte buffer. After the ligand was fixed, antibodies of c-Met, A8, A11 and C8 were bound, and the binding ability was evaluated by analyzing the Kon and Koff values.

Cell Culture and Antibody Therapy

H596 cells were cultured using RPMI (Wellgene) containing 10% FBS and 1% penicillin/streptomycin (Hyclone). In order to observe whether the antibody can induce a phosphorylation signal, the cells were cultured in a 6-well plate. Then, in order to remove the interference of the signal by FBS, it was cultured in RPMI medium without FBS overnight. The next day, the medium was removed, and a solution containing antibodies or HGF at different concentrations was treated for 1 hour.

Western Blot

After culturing the cells as described above, cells were obtained using a lysis buffer containing RIPA (Biosesang), a protease inhibitor (Roche), and a phosphatase inhibitor (Roche), cells were lysed using a 1 ml syringe. After lysis, the cells were centrifuged at 14000 rpm for 15 minutes. Then, a supernatant was obtained, and protein was quantified through the BCA analysis (Thermofisher) method. The supernatant was mixed with 5× sample loading buffer and then heated for 10 minutes. Then, SDS-PAGE was performed, and then the protein was transferred to the activated PVDF (polyvinylidene difluoride) apa brain (Bio-rad). Membrane activity was inhibited with 5% BSA, followed by reaction with a primary antibody, followed by reaction with a secondary antibody conjugated with Hrp. Then, it was confirmed using ECL (Amersham) in a dark room.

Cell Proliferation Assay

H596 cells were cultured overnight at a concentration of $1.0 \times 10^4$ cells/well in a 96-well plate. The next day, the medium was removed, and a solution containing HGF or anti-c-Met antibody was treated at a concentration of 39 picomolar to 10 nanomolar. Then, the cells were cultured for 72 hours, and the medium was replaced with a WST solution (DoGen) and cultured for 2-3 hours. Then, it was measured at 450 nm using a multi-reader (Tecan).

Example 1: Screening and Identification of scFv Binding to c-Met

Figure 1B:
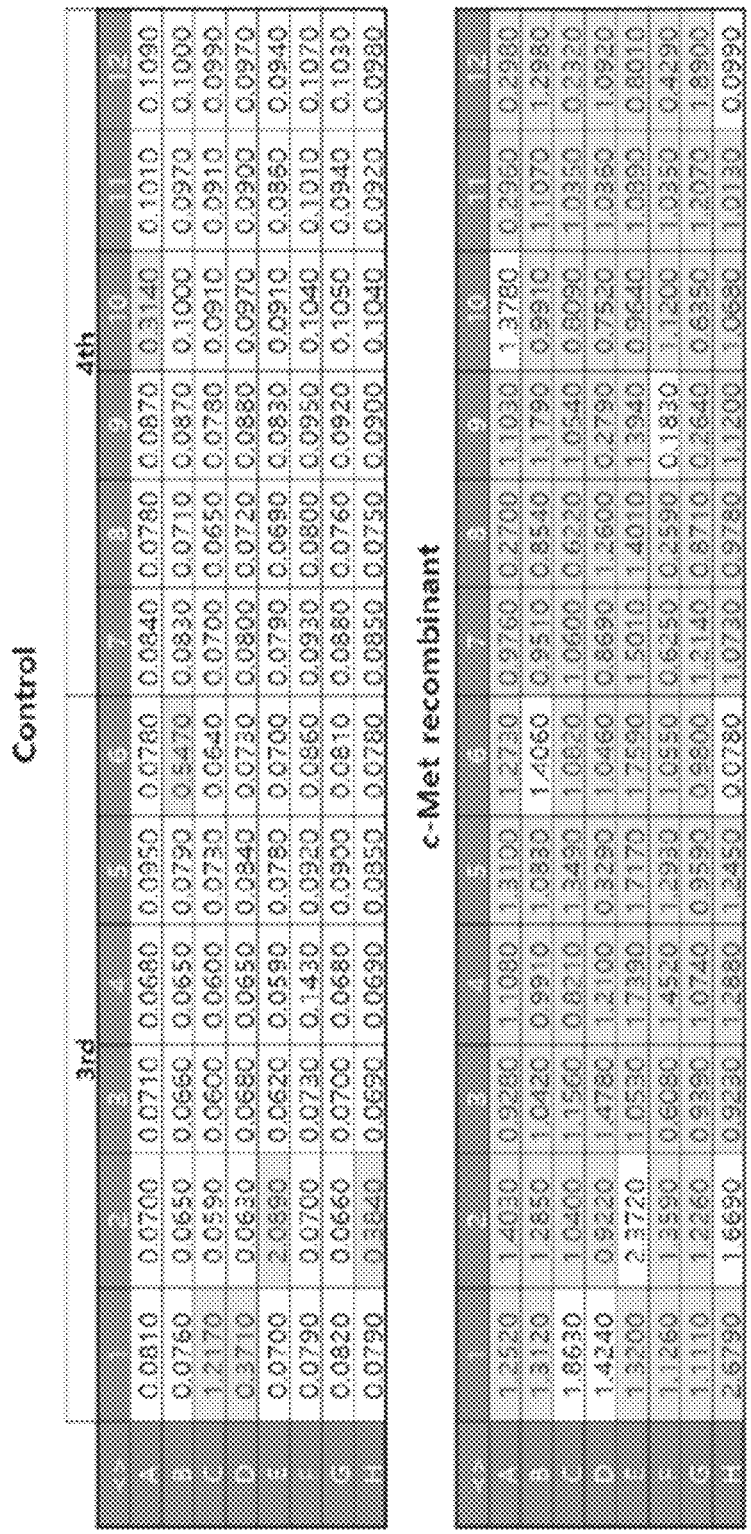
Figure 2:
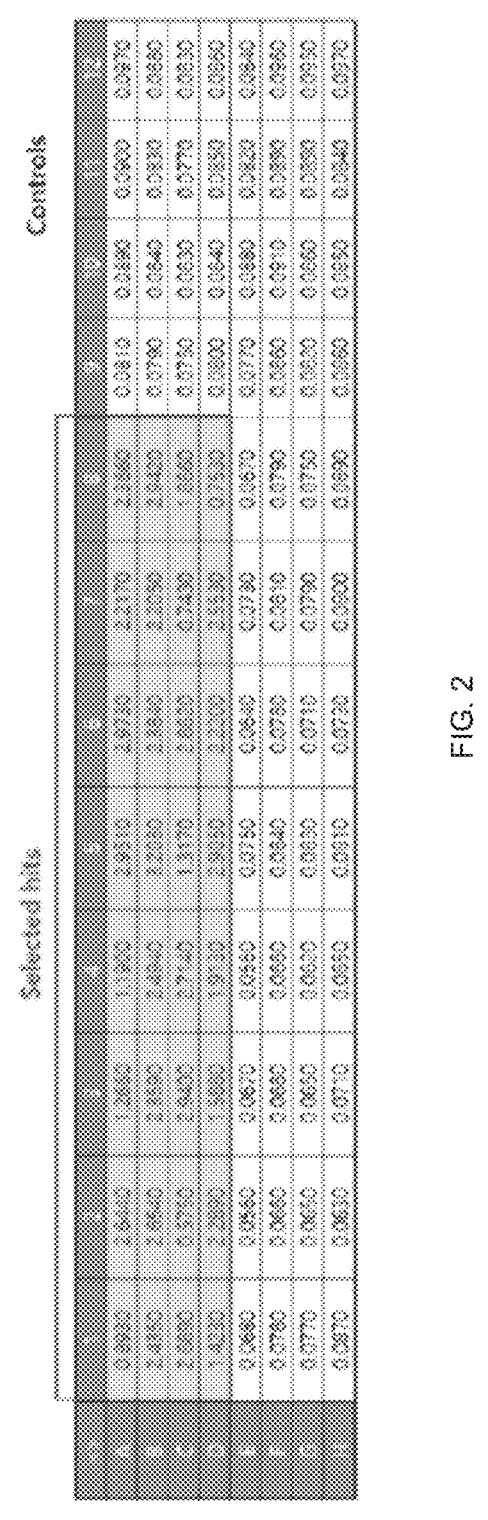

In order to identify the antibody that binds to c-Met, human scFv library screening was performed according to the method described above using a human recombinant c-Met antibody containing only an extracellular domain (aa, 1-932) as an antigen. The antigen was bound to an immunotube and 4 cycles were repeated. As a result, as shown in FIG. 1a, it was found that the output increased in the 3rd and 4th cycles, and the samples obtained in the 3rd and 4th cycles were confirmed for binding strength through ELISA method, and the result was shown in FIG. 1b. In addition, after selecting the one representing the signal compared to the control plate, sequencing was performed, and among them, 31 hits having different sequences were selected, and again ELISA was performed to confirm the binding strength, and then the ten most strongly binding candidates (hits) were selected. Each candidate was named A8, A9, A11, B8, B10, C8, C9, D7, D12, E10 based on the ELISA results. Then, 10 hits were converted to human IgG form (FIG. 2).

Example 2: Confirmation of Natural c-Met Binding of Human IgG Form

In order to confirm that the human IgG prepared in Example 1 binds to natural c-Met, an experiment was conducted as follows. First, 293F cells were transfected with plasmids according to the above experimental method and cultured for 7 days. Then, cells were obtained, and the antibody was purified using protein A beads, followed by SDS-PAGE.

Figure 3:
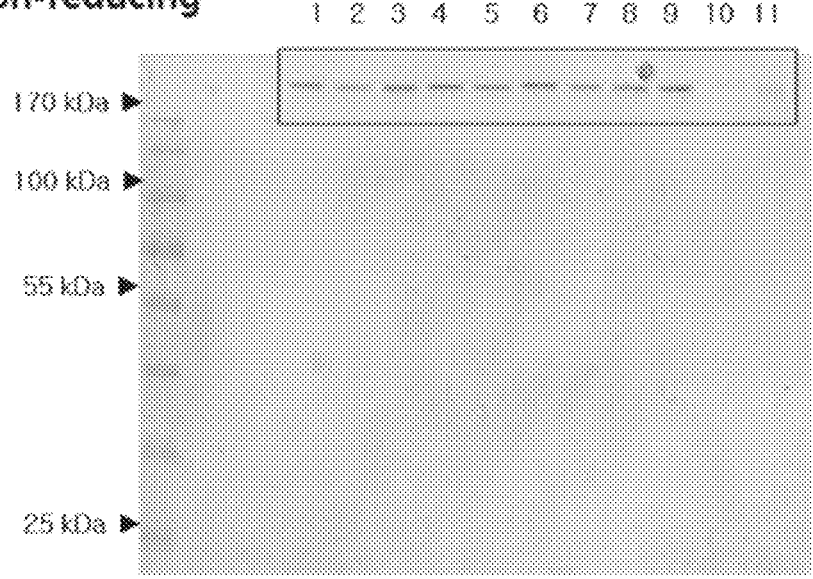
FIG. 3 shows the results of SDS-PAGE to confirm the size of the heavy and light chains of the purified antibody.
Figure 3:
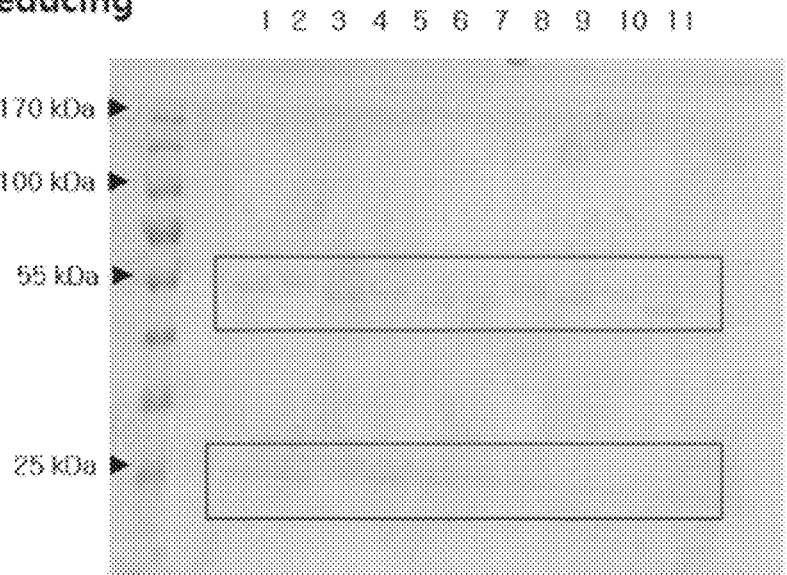

As a result, as shown in FIG. 3, it was confirmed that the ten most strongly bound hits in Example 1 were converted into human IgG form and expressed in cells, and the sizes of the light and heavy chains were confirmed.

After confirming that the IgG was converted, cells positive for c-Met were selected based on the information of CCLE, and flow cytometry was performed according to the above experimental method.

Figure 4A:
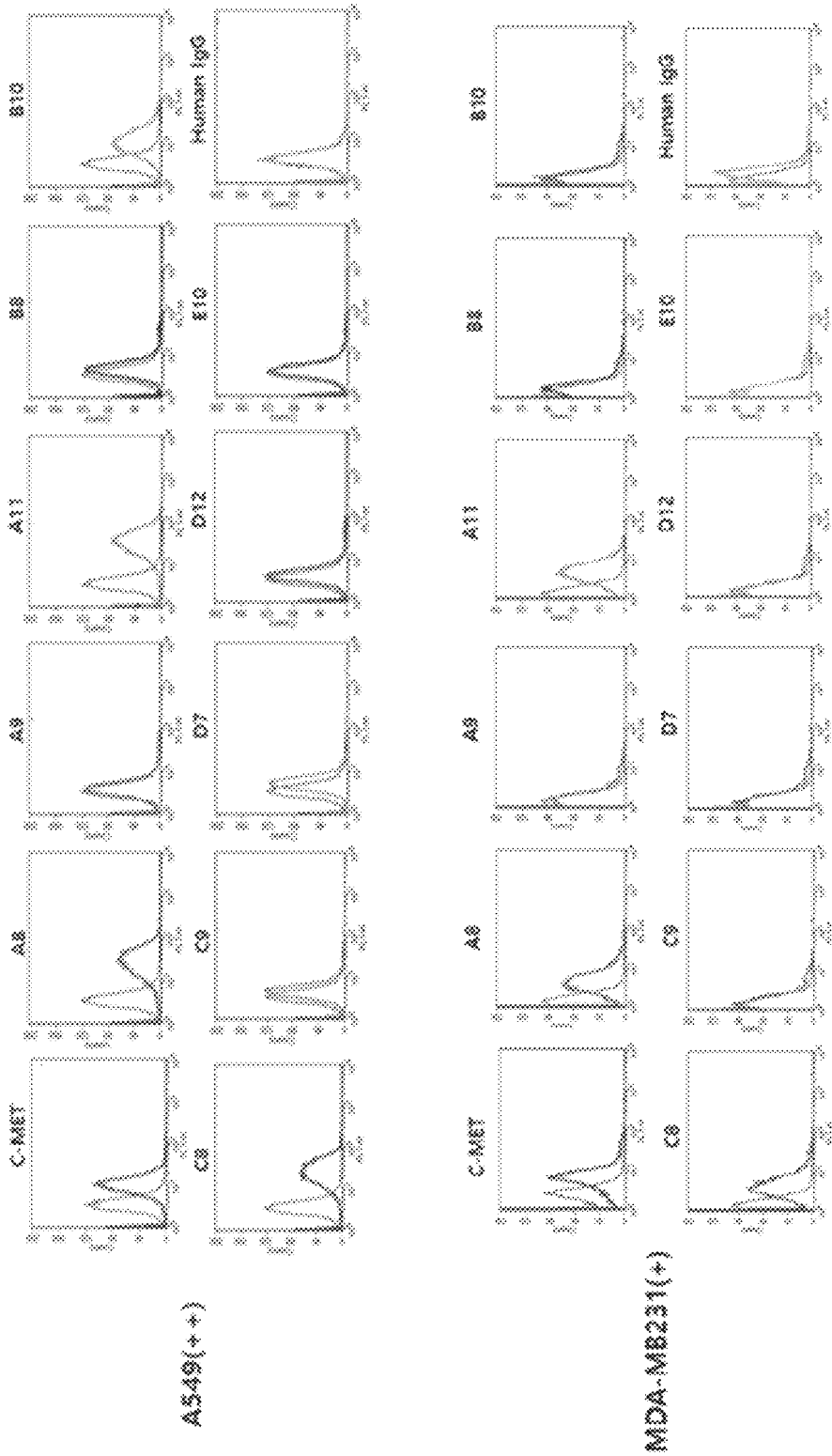
FIGS. 4a and 4b show the results of confirming the binding strength of 10 c-Met antibodies by flow cytometry using A549 cells and MDA-MB-231 cells (FIG. 4a) and the results of confirming the binding strength of c-Met antibodies (A8, A11, B10, C8) by flow cytometry using A549, H596 and SKBR-3 cells (FIG. 4b).

As a result, as shown in FIG. 4a, the binding pattern of the antibody was found to match the highest change in A549 cells and the expression level of c-Met, among them, the four antibodies that appeared most similar were selected and the same experiment was performed using different cell lines. At this time, the H596 cell line was an intermediate expression cell line, and the SKBR-3 cell line was used as a negative control.

Figure 4B:
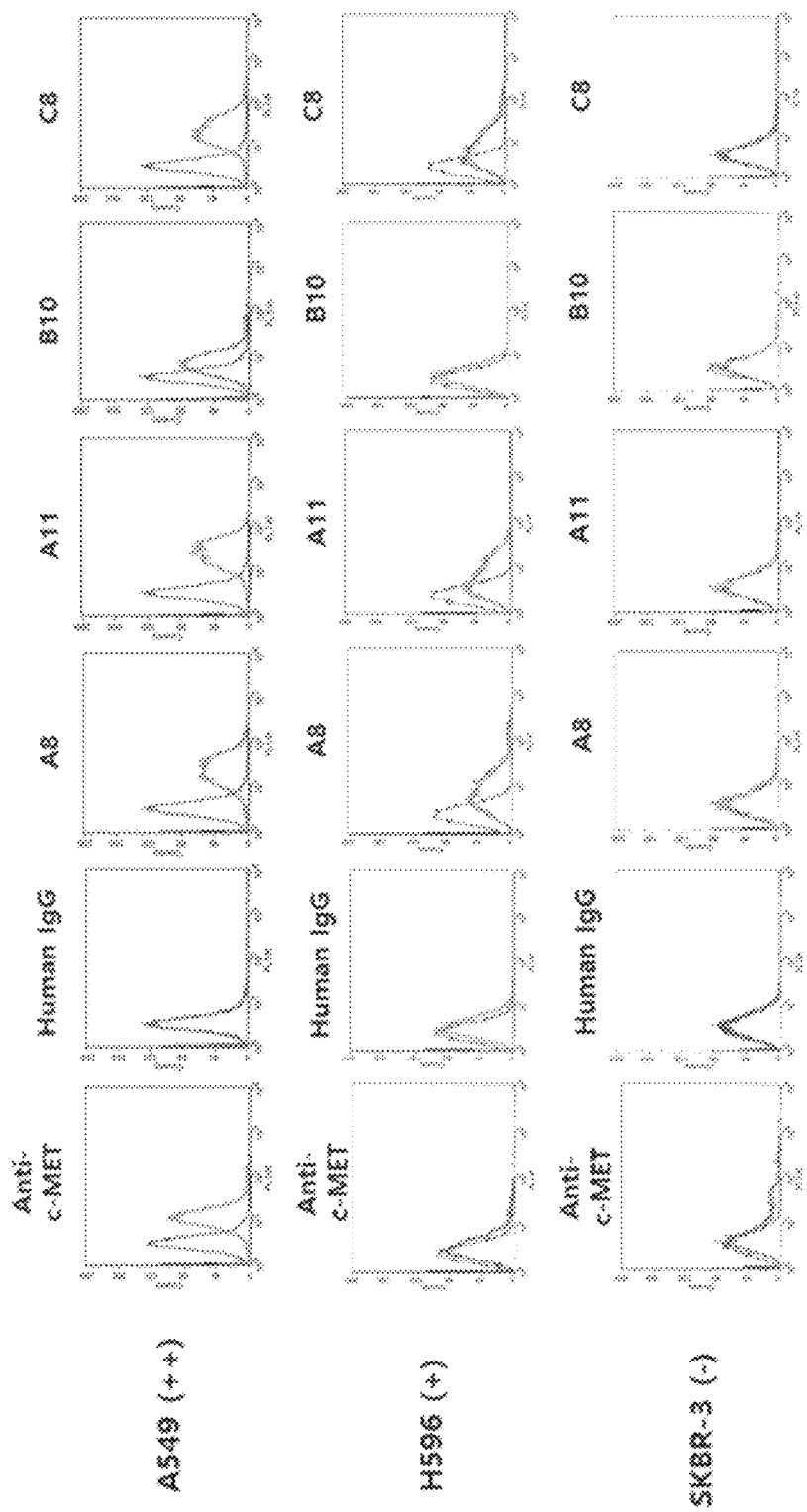

As a result, as shown in FIG. 4b, it was found that the binding pattern of the four antibodies (A8, A11, B10, C8) is related to the c-Met expression level, in the SKBR-3 cell line, a c-Met negative cell line, binding migration was not observed well. Among these, A8 was confirmed that the expression pattern of the control anti-c-Met antibody was similar in the A549 and H596 cell lines, it was confirmed that the SKBR-3 cell line was consistent with the expression rate of the control anti-c-Met antibody.

Through this, it was confirmed that the selected four leads have specificity for the c-Met receptor.

Example 3: Analysis of Binding Affinity of Lead Antibody

Based on the result of confirming the binding of the antibody to the natural c-Met in Example 2, an experiment was conducted as follows using the reads (A8, A11 and C8) showing the highest migration.

According to the above experimental method, the human c-Met recombinant protein, which is an antigen, was immobilized on a biosurface, and then the antibody was flowed to react with the antigen. Then, KD, which is a quantitative value for affinity, was calculated using the binding coefficient Kon and the dissociation coefficient Koff. Analysis was carried out on the Octat platform. The higher the Kon value, the faster the antibody and ligand bind, the lower the Koff value, the slower the dissociation occurs. The KD value was calculated as the ratio between Kon and Koff.

Figure 5:
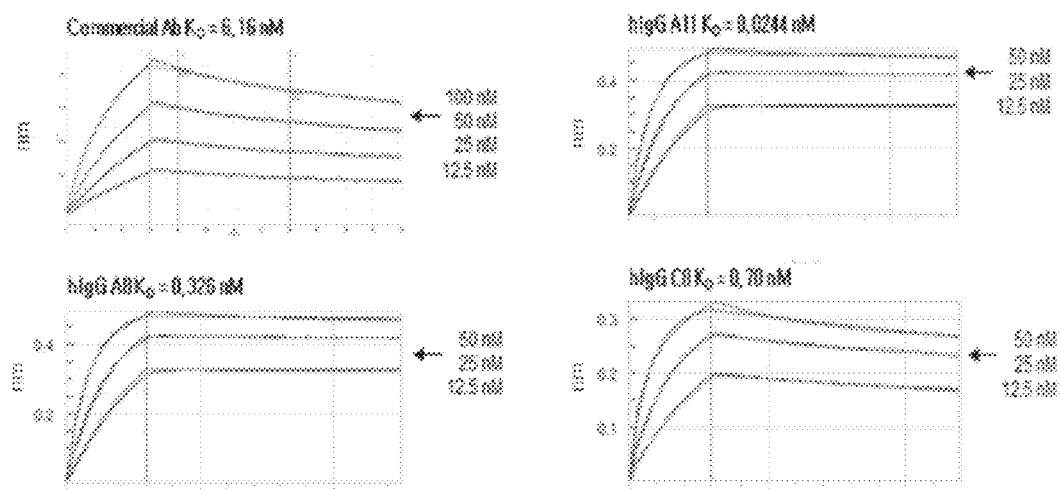
FIG. 5 shows the results of confirming the binding affinity of c-Met antibodies (A8, A11, B10, C8) using octet analysis.

As a result, as shown in FIG. 5, all three antibodies were found to have high affinity and dissociation values compared to the existing c-Met antibody. Among them, it was found that A8 has a KD value of 0.326 nM, and the affinity was found to be higher than that of the c-Met antibody.

Through this, it was confirmed that the A8 antibody binds faster and dissociates slowly from the receptor compared to the conventional c-Met antibody.

Example 4: Agonist Effect of c-Met Antibody

In order to confirm the effect of the c-Met antibody selected in the above example on signal transduction, an experiment was conducted as follows using a cell line positive for c-Met and dependent on HGF signal activity.

First, after culturing several cell lines positive for c-Met (Hs746T, H596, AsPC1, MKN45, SNU620, SNU5), respectively, proteins were obtained. Then, Western blot was performed as described in the experimental method, and the c-Met signal pattern was confirmed.

Figure 6A:
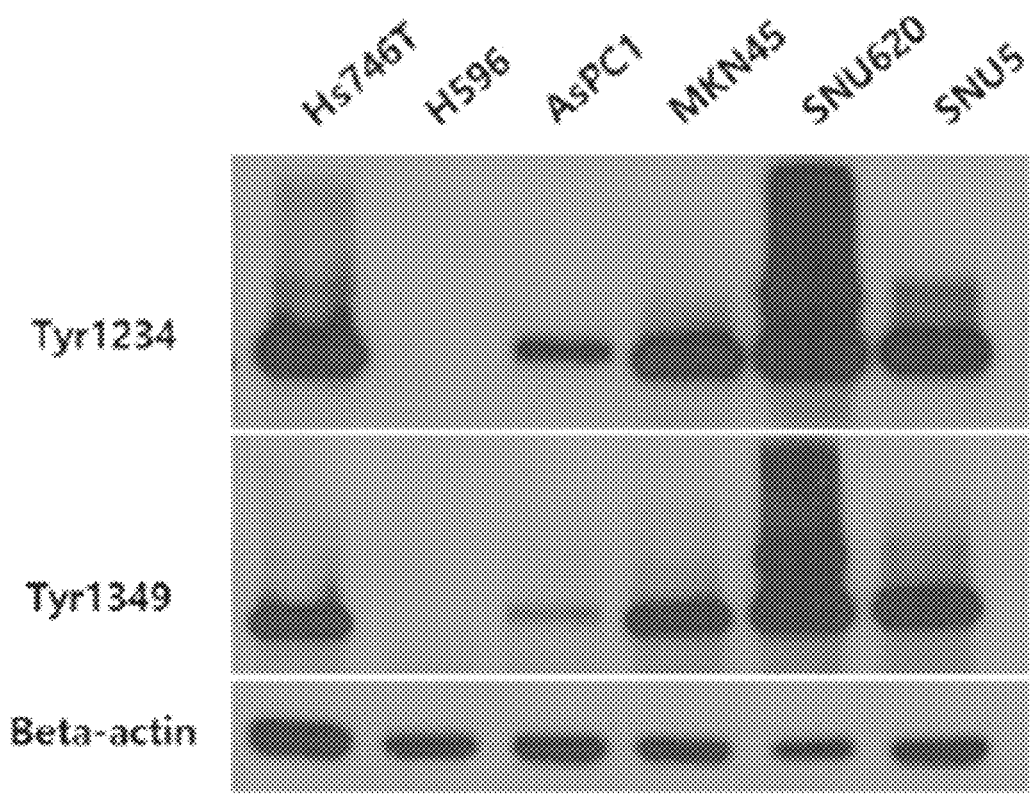
FIGS. 6a to 6c show the results of confirming the c-Met signal pattern in a c-Met positive cell line using a western blot method (FIG. 6a), the results of confirming the c-Met signal pattern by treating different concentrations of HGF in H596 cells (FIG. 6b) and the results of confirming the c-Met signal pattern by treating HGF and c-Met antibodies (A8, A11, B10, C8) in H596 cells (FIG. 6c).

As a result, as shown in FIG. 6a, it was found that phosphorylation of the c-Met catalyst did not occur only in the H596 cell line.

Figure 6B:
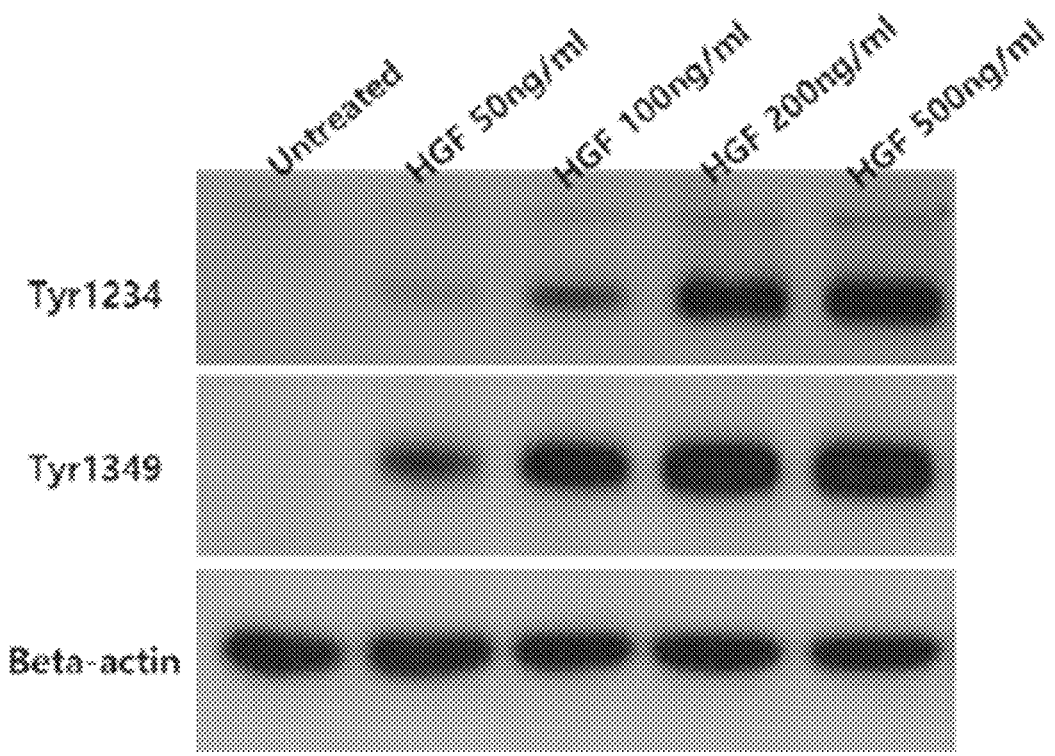

Thus, 50, 100, 200, 500 ng/ml of HGF was added to H596 cells, and Western blot was performed in the same manner. As a result, as shown in FIG. 6b, when HGF was added, the expression levels of Tyr1234 and Tyr1349 were found to increase in a concentration-dependent manner.

In addition, H596 cells were incubated overnight in RPMI medium (serum free) in a 6-well plate, and then treated with HGF and c-Met antibodies A8, A11, B10, and C8 at a nanomolar concentration for 1 hour. Then, cells were obtained and Western blot was performed in the same manner as above.

Figure 6C:
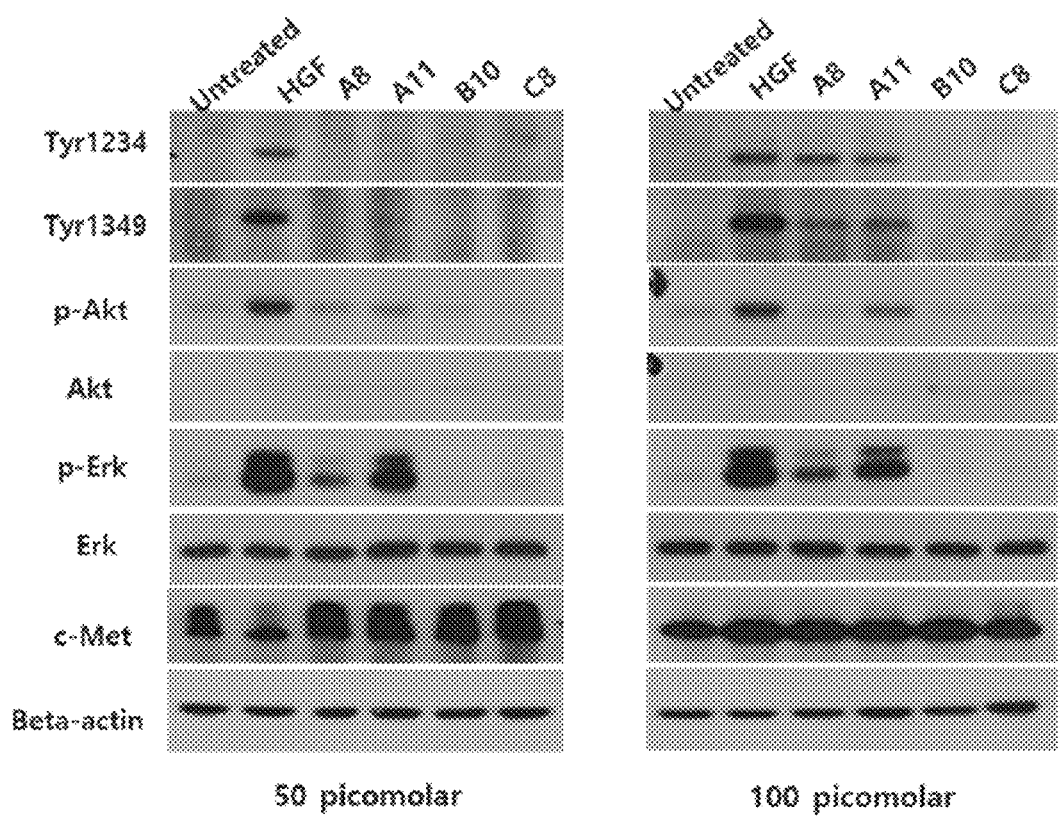

As a result, as shown in FIG. 6c, HGF, A8, and A11 were found to induce phosphorylation signals including major downstream signals such as p-Erk and p-Akt, but not B10 and C8. In addition, when A8 was treated, the expression levels of Tyr1234 and Tyr1349 were found to increase in a concentration-dependent manner, and the expression of p-Erk and p-Akt was found to be induced.

Example 5: Effect of c-Met Antibody on Cell Proliferation

In order to confirm the effect of the signal induction of the c-Met antibody identified in Example 4 directly on cells, an experiment was conducted as follows.

First, H596 cells were cultured in a 96-well plate, and HGF, A8, or A11, which induced signal activity in Example 4, was treated at a concentration of 0.039 to 10 nM. Then, the cells were further cultured for 72 hours, and cell proliferation was analyzed by the WST assay method. The value was calculated in proportion to the cell growth rate of the control group (untreated).

Figure 7:
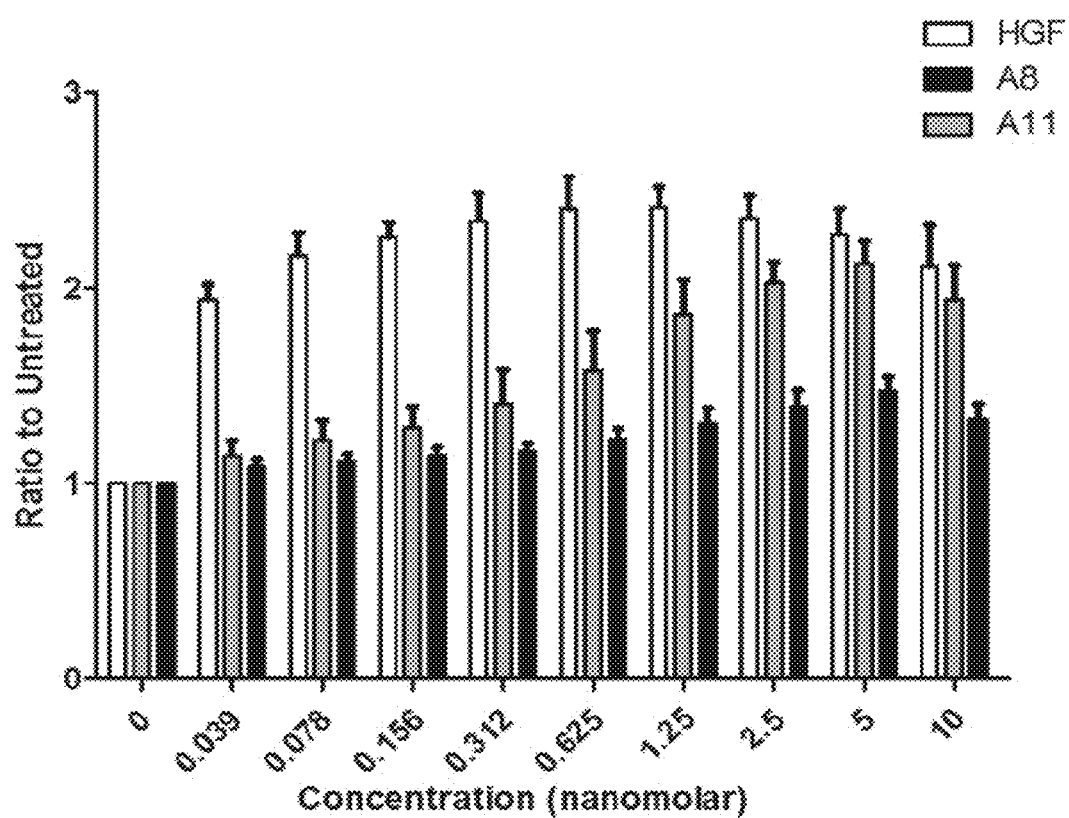
FIG. 7 shows the results of confirming the effect of c-Met antibody and HGF on cell proliferation using the WST analysis method.

As a result, as shown in FIG. 7, it was confirmed that the cells proliferated when HGF, A8 or A11 was treated, in the case of treatment with the A8 antibody, the same cell proliferation rate as in the case of HGF treatment was not observed, but the saturation point was higher.

Example 6: Effect of c-Met Antibody on Mesenchymal Stem Cells

In order to confirm that the c-Met antibodies A8 and A11 exhibit the same effect as HGF in mesenchymal stem cells, an experiment was conducted as follows.

In a 6-well plate, a medium containing growth factors and chemically stable was added, and mesenchymal stem cells were inoculated. In this case, a medium without HGF, a medium containing different concentrations of HGF, A8, or A11 was used.

6-1: Cytotoxic Effect of c-Met Antibody

According to the above experimental method, adipose derived mesenchymal stem cells were treated with HGF, A8, or A11 at different concentrations, and cultured in a medium from which HGF was removed. During cultivation, medium time, viability, and cell morphology were evaluated, and using a Cedes cell counter (Roche, USA), population doubling time and viability were evaluated through counting after trypan blue staining, and cell morphology was observed by taking an image using an optical microscope.

Figure 8A:
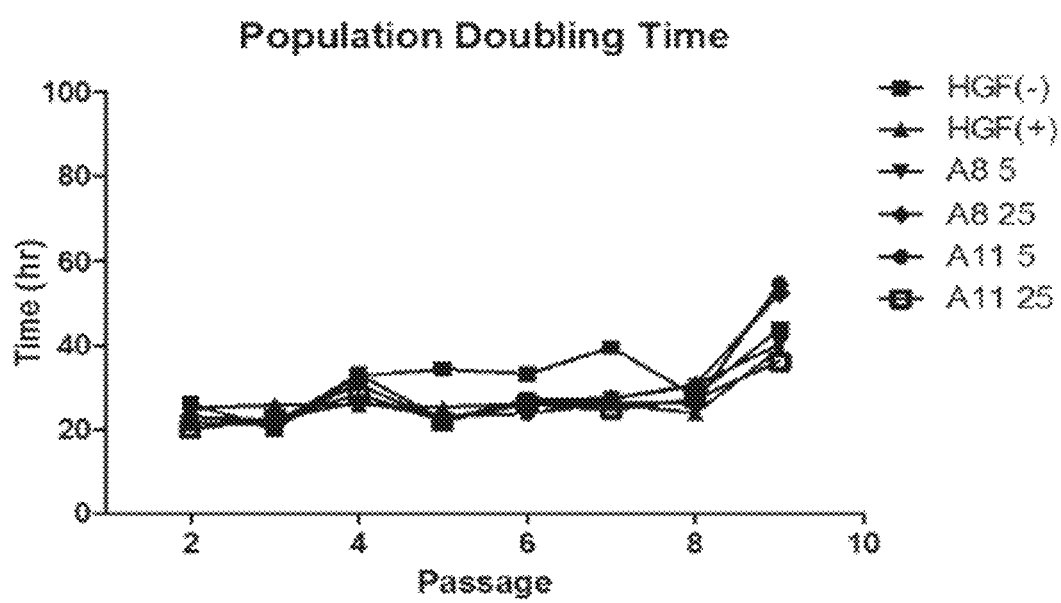
FIGS. 8a and 8b show the results of confirming the effect of HGF or c-Met antibody (A8) on the population doubling time (FIG. 8a) and viability (FIG. 8b) of mesenchymal stem cells.
Figure 8B:
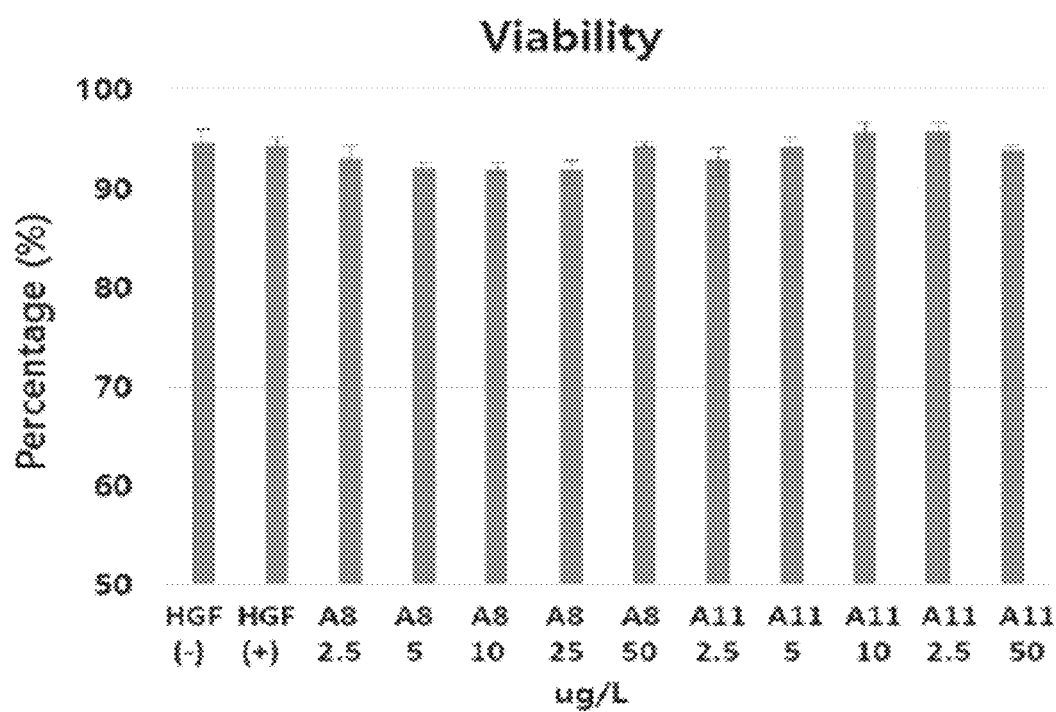
Figure 9A:
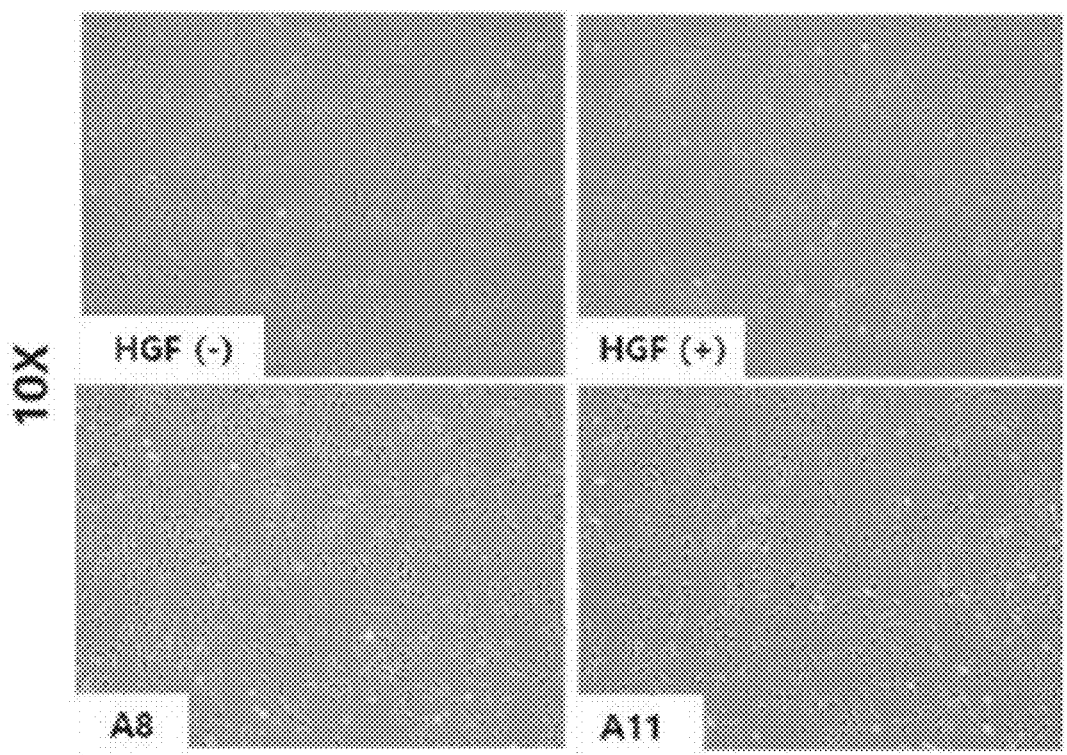
FIG. 9A to 9D show the result of confirming the effect of HGF or c-Met antibodies (A8) in culture form (FIG. 9a) and adipocyte differentiation (FIG. 9b), cartilage differentiation (FIG. 9c) and bone differentiation (FIG. 9d) according to culture conditions of mesenchymal stem cells.
Figure 9B:
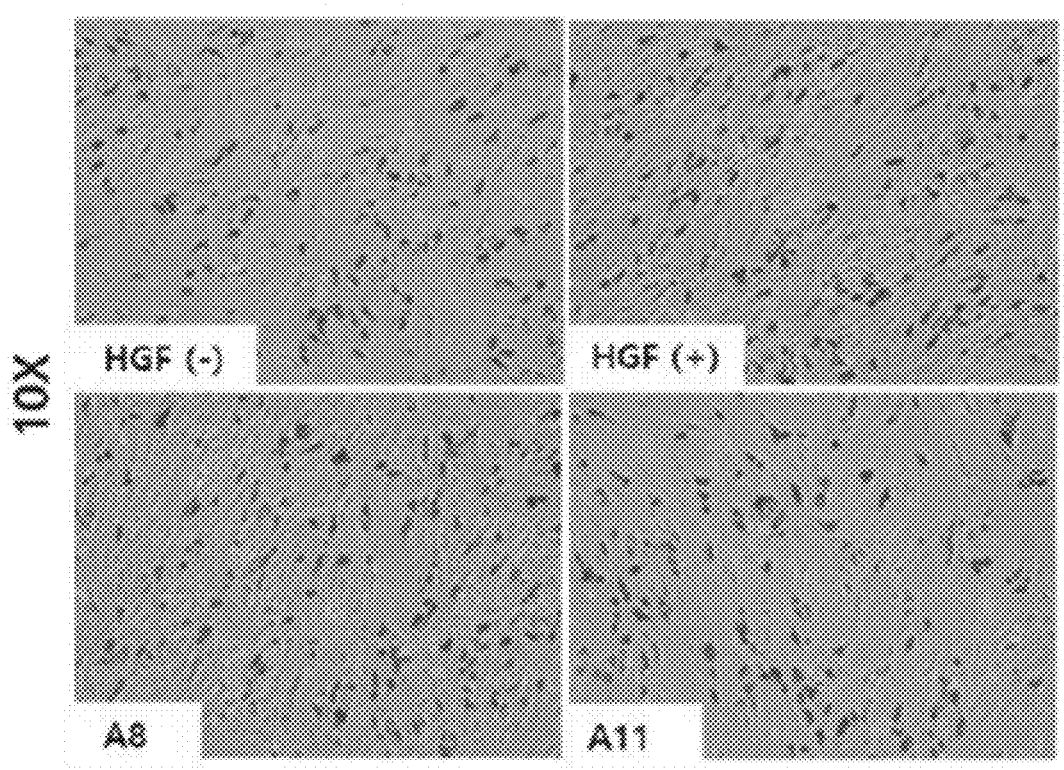
Figure 9C:
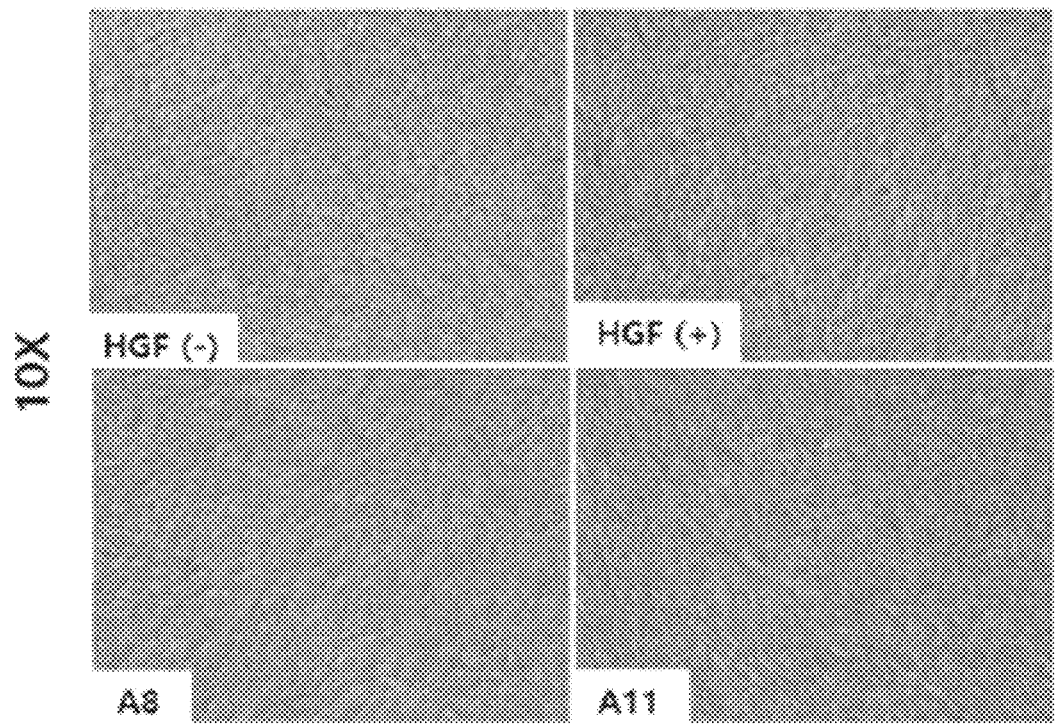
Figure 9D:
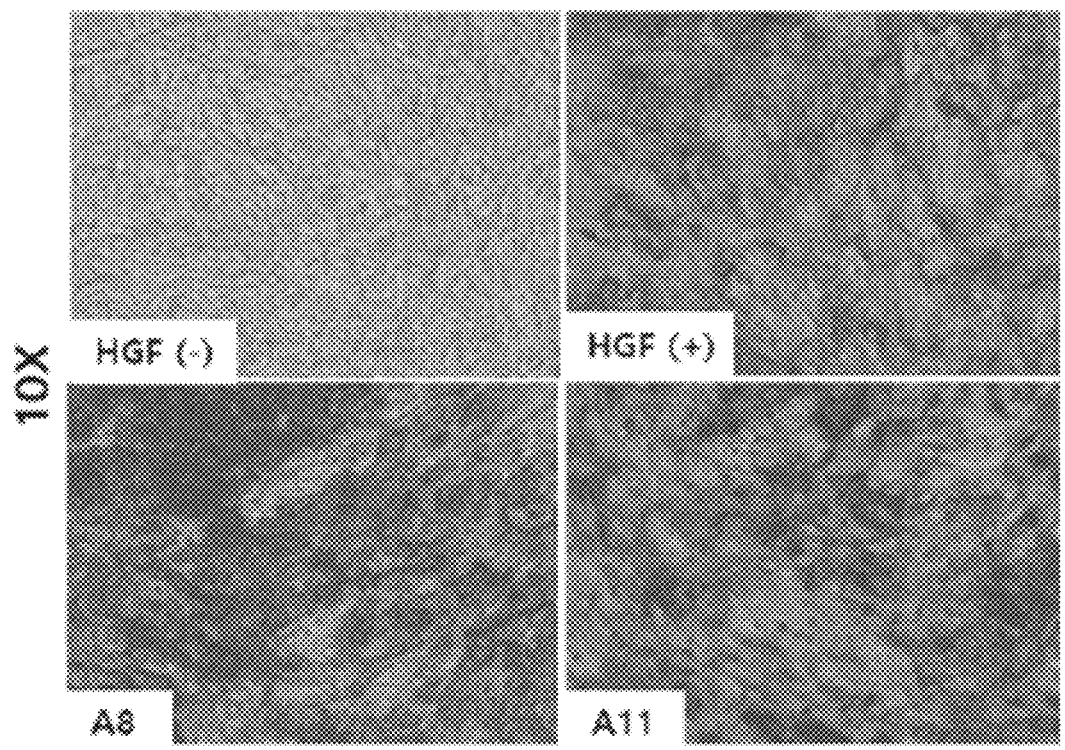

As a result, as shown in FIGS. 8a and 8b, the population doubling time did not show a significant difference between the case of not treating HGF and the case of treating HGF and c-Met antibody A8. In addition, it was found that the average survival rate of cells was more than 90% in all groups.

Through this, it was confirmed that the c-Met antibody A8 did not affect the culture form of stem cells, and had similar effects to HGF.

6-2: Effect of c-Met Antibody on Stem Cell Differentiation

According to the above experimental method, Adipose derived mesenchymal stem cells were cultured in various control media until passage 9. Cells were inoculated into 6 well plates in passage 9, and then grown according to the cell lineage to be differentiated. Cells were induced to adipose, cartilage and bone differentiation.

First, it was differentiated into adipocytes in the following manner. When the cells grew to about 90-100% in passage 10, the culture medium was replaced with a cell differentiation medium. StemPro adipogenesis differentiation kit (Thermofisher, USA) was used as a differentiation medium, and the medium was changed every 2-3 days and maintained for 2-3 weeks. After differentiated into fat, cells were observed by staining with Oil red O to observe the cells.

In addition, stem cells were differentiated into chondrocytes by the following method. When the cells grew to about 50% in passage 10, the culture medium was replaced with a medium for cell differentiation. DMEM low glucose medium (Wellgene, Korea) containing FBS (Hyclone, USA), 1% ITS-X, 50 ug/ml ascorbic acid, 100 nM dexamethasone and 10 ng/ml TGF-β1 was used as a differentiation of medium, and the medium was changed every 2-3 days and maintained for 2-3 weeks. After 3 weeks, the cells were fixed and observed by staining with Alcian Blue.

In addition, stem cells were differentiated into bone cells by the following method. After culturing the cells until passage 10, the culture medium was replaced with a medium for cell differentiation. DMEM low glucose medium (Wellgene, Korea) containing FBS, 100 nM dexamethasone, 10 nM glycerol-2-phosphate, 50 ug/ml ascorbic acid and 1% Glutamax was used as a differentiation medium, and the medium was changed every 2-3 days and maintained for 3 weeks. After 3 weeks, the cells were fixed and observed by staining with Alizarin Red solution.

As a result, as shown in FIGS. 9a to 9d, stem cells were found to differentiate into adipocytes in all medium conditions, but cartilage and bone differentiation did not differentiate in HGF-free medium. In addition, it was found that cells cultured in a medium containing A8 were stained at a density similar to that of the HGF control.

Through this, it was confirmed that HGF plays an important role in maintaining stem cell multipotency, and it was confirmed that A8 plays the same role as HGF in stem cells.

INDUSTRIAL APPLICABILITY

As described above, the present invention provides an anti-c-Met agonist antibody and use thereof. The method of the present invention can be usefully used for detecting c-Met antibodies, inducing stem cell differentiation using the antibody, and treating or preventing cancer.

---

What is claimed is:

1. An agonist antibody or fragment thereof that specifically binds to a human-derived c-Met protein comprising an antibody light chain variable region (VL) comprising a complementarity determining region (CDR) L1 containing the amino acid sequence defined by SEQ ID NO: 1, a complementarity determining region (CDR) L2 containing the amino acid sequence defined by SEQ ID NO: 2 and a complementarity determining region (CDR) L3 containing the amino acid sequence defined by SEQ ID NO: 3, and an antibody heavy chain variable region (VH) comprising a complementarity determining region (CDR) H1 containing the amino acid sequence defined by SEQ ID NO: 4, a complementarity determining region (CDR) H2 containing the amino acid sequence defined by SEQ ID NO: 5 and a complementarity determining region (CDR) H3 containing the amino acid sequence defined by SEQ ID NO: 6.

2. The agonist antibody or fragment thereof of claim 1, wherein the fragment is a fragment selected from the group consisting of diabody, Fab, Fab', F(ab)2, F(ab')2, Fv, and scFv.

3. A polynucleotide encoding the antibody or a fragment thereof of claim 1.

4. A vector comprising the polynucleotide of claim 3.

5. A cell transformed with the vector of claim 4.

6. A method for producing an agonist antibody or fragment thereof for binding to human c-Met, the method comprising culturing the cell of claim 5 under conditions in which the polynucleotide is expressed to produce a polypeptide comprising a light chain variable region and a heavy chain variable region, and recovering the polypeptide from the cell or a culture medium in which the same is cultured.

7. A c-Met-specific detection method comprising contacting the antibody or fragment thereof of claim 1 with a sample, and detecting the agonist antibody or fragment thereof.

8. A composition for inducing stem cell differentiation comprising the antibody of claim 1.

9. The composition according to claim 8, wherein the stem cell is a fat-derived mesenchymal stem cell.

10. A culture medium for stem cells comprising the composition of claim 8.

11. A method for inducing stem cell differentiation comprising administering an effective amount of a composition comprising the antibody of claim 1 to a subject in need thereof.

* * * * *

SEQUENCE LISTING

<160> NUMBER OF SEQ ID NOS: 8

<210> SEQ ID NO 1
<211> LENGTH: 13
<212> TYPE: PRT
<213> ORGANISM: Artificial Sequence
<220> FEATURE:
<223> OTHER INFORMATION: VL-CDR1 of c-Met A8

<400> SEQUENCE: 1

Thr Gly Ser Ser Ser Asn Ile Gly Asn Asn Asn Val Tyr
1               5                   10

<210> SEQ ID NO 2
<211> LENGTH: 7
<212> TYPE: PRT

```
<213> ORGANISM: Artificial Sequence
<220> FEATURE:
<223> OTHER INFORMATION: VL-CDR2 of c-Met A8

<400> SEQUENCE: 2

Ala Asn Ser His Arg Pro Ser
1               5

<210> SEQ ID NO 3
<211> LENGTH: 9
<212> TYPE: PRT
<213> ORGANISM: Artificial Sequence
<220> FEATURE:
<223> OTHER INFORMATION: VL-CDR3 of c-Met A8

<400> SEQUENCE: 3

Gly Ser Trp Asp Tyr Ser Leu Asn Gly
1               5

<210> SEQ ID NO 4
<211> LENGTH: 5
<212> TYPE: PRT
<213> ORGANISM: Artificial Sequence
<220> FEATURE:
<223> OTHER INFORMATION: VH-CDR1 of c-Met A8

<400> SEQUENCE: 4

Asp Tyr Tyr Met Ser
1               5

<210> SEQ ID NO 5
<211> LENGTH: 17
<212> TYPE: PRT
<213> ORGANISM: Artificial Sequence
<220> FEATURE:
<223> OTHER INFORMATION: VH-CDR2 of c-Met A8

<400> SEQUENCE: 5

Ala Ile Ser His Asp Asp Ser Ser Ile Tyr Tyr Ala Asp Ser Val Lys
1               5                   10                  15

Gly

<210> SEQ ID NO 6
<211> LENGTH: 18
<212> TYPE: PRT
<213> ORGANISM: Artificial Sequence
<220> FEATURE:
<223> OTHER INFORMATION: VH-CDR3 of c-Met A8

<400> SEQUENCE: 6

Asp Leu Leu Gln Cys Asn Ser Glu Gln Cys Tyr Ser Asp Asn Gly Met
1               5                   10                  15

Asp Val

<210> SEQ ID NO 7
<211> LENGTH: 1408
<212> TYPE: PRT
<213> ORGANISM: Artificial Sequence
<220> FEATURE:
<223> OTHER INFORMATION: Homo sapiens c-Met Protein

<400> SEQUENCE: 7

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
```

```
                20                  25                  30
        Ser Glu Met Asn Val Asn Met Lys Tyr Gln Leu Pro Asn Phe Thr Ala
                    35                  40                  45

Glu Thr Pro Ile Gln Asn Val Ile Leu His Glu His Ile Phe Leu
            50                  55                  60

Gly Ala Thr Asn Tyr Ile Tyr Val Leu Asn Glu Asp Leu Gln Lys
        65                  70                  75                  80

Val Ala Glu Tyr Lys Thr Gly Pro Val Leu His Pro Asp Cys Phe
                        85                  90                  95

Pro Cys Gln Asp Cys Ser Ser Lys Ala Asn Leu Ser Gly Gly Val Trp
                    100                 105                 110

Lys Asp Asn Ile Asn Met Ala Leu Val Val Asp Thr Tyr Tyr Asp Asp
                    115                 120                 125

Gln Leu Ile Ser Cys Gly Ser Val Asn Arg Gly Thr Cys Gln Arg His
                    130                 135                 140

Val Phe Pro His Asn His Thr Ala Asp Ile Gln Ser Glu Val His Cys
        145                 150                 155                 160

Ile Phe Ser Pro Gln Ile Glu Glu Pro Ser Gln Cys Pro Asp Cys Val
                        165                 170                 175

Val Ser Ala Leu Gly Ala Lys Val Leu Ser Ser Val Lys Asp Arg Phe
                    180                 185                 190

Ile Asn Phe Phe Val Gly Asn Thr Ile Asn Ser Ser Tyr Phe Pro Asp
                    195                 200                 205

His Pro Leu His Ser Ile Ser Val Arg Arg Leu Lys Glu Thr Lys Asp
                    210                 215                 220

Gly Phe Met Phe Leu Thr Asp Gln Ser Tyr Ile Asp Val Leu Pro Glu
        225                 230                 235                 240

Phe Arg Asp Ser Tyr Pro Ile Lys Tyr Val His Ala Phe Glu Ser Asn
                        245                 250                 255

Asn Phe Ile Tyr Phe Leu Thr Val Gln Arg Glu Thr Leu Asp Ala Gln
                    260                 265                 270

Thr Phe His Thr Arg Ile Ile Arg Phe Cys Ser Ile Asn Ser Gly Leu
                    275                 280                 285

His Ser Tyr Met Glu Met Pro Leu Glu Cys Ile Leu Thr Glu Lys Arg
                    290                 295                 300

Lys Lys Arg Ser Thr Lys Lys Glu Val Phe Asn Ile Leu Gln Ala Ala
        305                 310                 315                 320

Tyr Val Ser Lys Pro Gly Ala Gln Leu Ala Arg Gln Ile Gly Ala Ser
                        325                 330                 335

Leu Asn Asp Asp Ile Leu Phe Gly Val Phe Ala Gln Ser Lys Pro Asp
                    340                 345                 350

Ser Ala Glu Pro Met Asp Arg Ser Ala Met Cys Ala Phe Pro Ile Lys
                    355                 360                 365

Tyr Val Asn Asp Phe Phe Asn Lys Ile Val Asn Lys Asn Asn Val Arg
                    370                 375                 380

Cys Leu Gln His Phe Tyr Gly Pro Asn His Glu His Cys Phe Asn Arg
        385                 390                 395                 400

Thr Leu Leu Arg Asn Ser Ser Gly Cys Glu Ala Arg Arg Asp Glu Tyr
                        405                 410                 415

Arg Thr Glu Phe Thr Thr Ala Leu Gln Arg Val Asp Leu Phe Met Gly
                    420                 425                 430

Gln Phe Ser Glu Val Leu Leu Thr Ser Ile Ser Thr Phe Ile Lys Gly
                    435                 440                 445
```

```
Asp Leu Thr Ile Ala Asn Leu Gly Thr Ser Glu Gly Arg Phe Met Gln
450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
            515                 520                 525

Cys Leu Ser Ala Pro Pro Phe Val Gln Cys Gly Trp Cys His Asp Lys
            530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
            595                 600                 605

Ser Cys Thr Leu Thr Leu Ser Glu Ser Thr Met Asn Thr Leu Lys Cys
610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
            675                 680                 685

His Ile Ser Ile Gly Gly Lys Thr Cys Thr Leu Lys Ser Val Ser Asn
            690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Thr Trp Trp Lys Glu Pro Leu Asn Ile Val Ser Phe Leu
            755                 760                 765

Phe Cys Phe Ala Ser Gly Gly Ser Thr Ile Thr Gly Val Gly Lys Asn
            770                 775                 780

Leu Asn Ser Val Ser Val Pro Arg Met Val Ile Asn Val His Glu Ala
785                 790                 795                 800

Gly Arg Asn Phe Thr Val Ala Cys Gln His Arg Ser Asn Ser Glu Ile
                805                 810                 815

Ile Cys Cys Thr Thr Pro Ser Leu Gln Gln Leu Asn Leu Gln Leu Pro
            820                 825                 830

Leu Lys Thr Lys Ala Phe Phe Met Leu Asp Gly Ile Leu Ser Lys Tyr
            835                 840                 845

Phe Asp Leu Ile Tyr Val His Asn Pro Val Phe Lys Pro Phe Glu Lys
            850                 855                 860
```

-continued

Pro Val Met Ile Ser Met Gly Asn Glu Asn Val Leu Glu Ile Lys Gly
865                 870                 875                 880

Asn Asp Ile Asp Pro Glu Ala Val Lys Gly Glu Val Leu Lys Val Gly
                885                 890                 895

Asn Lys Ser Cys Glu Asn Ile His Leu His Ser Glu Ala Val Leu Cys
                900                 905                 910

Thr Val Pro Asn Asp Leu Leu Lys Leu Asn Ser Glu Leu Asn Ile Glu
                915                 920                 925

Trp Lys Gln Ala Ile Ser Ser Thr Val Leu Gly Lys Val Ile Val Gln
            930                 935                 940

Pro Asp Gln Asn Phe Thr Gly Leu Ile Ala Gly Val Val Ser Ile Ser
945                 950                 955                 960

Thr Ala Leu Leu Leu Leu Leu Gly Phe Phe Leu Trp Leu Lys Lys Arg
                965                 970                 975

Lys Gln Ile Lys Asp Leu Gly Ser Glu Leu Val Arg Tyr Asp Ala Arg
                980                 985                 990

Val His Thr Pro His Leu Asp Arg Leu Val Ser Ala Arg Ser Val Ser
                995                 1000                1005

Pro Thr Thr Glu Met Val Ser Asn Glu Ser Val Asp Tyr Arg Ala
    1010                1015                1020

Thr Phe Pro Glu Asp Gln Phe Pro Asn Ser Ser Gln Asn Gly Ser
    1025                1030                1035

Cys Arg Gln Val Gln Tyr Pro Leu Thr Asp Met Ser Pro Ile Leu
    1040                1045                1050

Thr Ser Gly Asp Ser Asp Ile Ser Ser Pro Leu Leu Gln Asn Thr
    1055                1060                1065

Val His Ile Asp Leu Ser Ala Leu Asn Pro Glu Leu Val Gln Ala
    1070                1075                1080

Val Gln His Val Val Ile Gly Pro Ser Ser Leu Ile Val His Phe
    1085                1090                1095

Asn Glu Val Ile Gly Arg Gly His Phe Gly Cys Val Tyr His Gly
    1100                1105                1110

Thr Leu Leu Asp Asn Asp Gly Lys Lys Ile His Cys Ala Val Lys
    1115                1120                1125

Ser Leu Asn Arg Ile Thr Asp Ile Gly Glu Val Ser Gln Phe Leu
    1130                1135                1140

Thr Glu Gly Ile Ile Met Lys Asp Phe Ser His Pro Asn Val Leu
    1145                1150                1155

Ser Leu Leu Gly Ile Cys Leu Arg Ser Glu Gly Ser Pro Leu Val
    1160                1165                1170

Val Leu Pro Tyr Met Lys His Gly Asp Leu Arg Asn Phe Ile Arg
    1175                1180                1185

Asn Glu Thr His Asn Pro Thr Val Lys Asp Leu Ile Gly Phe Gly
    1190                1195                1200

Leu Gln Val Ala Lys Gly Met Lys Tyr Leu Ala Ser Lys Lys Phe
    1205                1210                1215

Val His Arg Asp Leu Ala Ala Arg Asn Cys Met Leu Asp Glu Lys
    1220                1225                1230

Phe Thr Val Lys Val Ala Asp Phe Gly Leu Ala Arg Asp Met Tyr
    1235                1240                1245

Asp Lys Glu Tyr Tyr Ser Val His Asn Lys Thr Gly Ala Lys Leu
    1250                1255                1260

Pro Val Lys Trp Met Ala Leu Glu Ser Leu Gln Thr Gln Lys Phe

Thr Thr Lys Ser Asp Val Trp Ser Phe Gly Val Leu Leu Trp Glu
1265                1270                1275

Leu Met Thr Arg Gly Ala Pro Pro Tyr Pro Asp Val Asn Thr Phe
1280                1285                1290

Asp Ile Thr Val Tyr Leu Leu Gln Gly Arg Arg Leu Leu Gln Pro
1295                1300                1305

Glu Tyr Cys Pro Asp Pro Leu Tyr Glu Val Met Leu Lys Cys Trp
1310                1315                1320

His Pro Lys Ala Glu Met Arg Pro Ser Phe Ser Glu Leu Val Ser
1325                1330                1335

Arg Ile Ser Ala Ile Phe Ser Thr Phe Ile Gly Glu His Tyr Val
1340                1345                1350

His Val Asn Ala Thr Tyr Val Asn Val Lys Cys Val Ala Pro Tyr
1355                1360                1365

Pro Ser Leu Leu Ser Ser Glu Asp Asn Ala Asp Asp Glu Val Asp
1370                1375                1380

Thr Arg Pro Ala Ser Phe Trp Glu Thr Ser
1385                1390                1395

1400                1405

<210> SEQ ID NO 8
<211> LENGTH: 6710
<212> TYPE: DNA
<213> ORGANISM: Artificial Sequence
<220> FEATURE:
<223> OTHER INFORMATION: Homo sapiens c-Met mRNA

<400> SEQUENCE: 8
gcaggtgacc cggaggccct cgccgcccgc ggcgccccga gcgctttgtg agcagatgcg     60
gagccgagtg gagggcgcga gccagatgcg gggcgacagc tgacttgctg agaggaggcg    120
gggaggcgcg gagcgcgcgt gtggtccttg cgccgctgac ttctccactg gttcctgggc    180
accgaaagat aaacctctca taatgaaggc ccccgctgtg cttgcacctg catcctcgt     240
gctcctgttt accttggtgc agaggagcaa tgggagtgt aaagaggcac tagcaaagtc    300
cgagatgaat gtgaatatga agtatcagct tcccaacttc accgcggaaa cacccatcca    360
gaatgtcatt ctacatgagc atcacatttt ccttggtgcc actaactaca tttatgtttt    420
aaatgaggaa gaccttcaga aggttgctga gtacaagact gggcctgtgc tggaacaccc    480
agattgtttc ccatgtcagg actgcagcag caaagccaat ttatcaggag tgtttggaa    540
agataacatc aacatggctc tagttgtcga cacctactat gatgatcaac tcattagctg    600
tggcagcgtc aacagaggga cctgccagcg acatgtcttt ccccacaatc atactgctga    660
catacagtcg gaggttcact gcatattctc cccacagata gaagagccca gccagtgtcc    720
tgactgtgtg gtgagcgccc tgggagccaa agtcctttca tctgtaaagg accggttcat    780
caacttcttt gtaggcaata ccataaattc ttcttatttc ccagatcatc cattgcattc    840
gatatcagtg agaaggctaa ggaaacgaa agatggtttt atgttttga cggaccagtc    900
ctacattgat gttttacctg agttcagaga ttcttacccc attaagtatg tccatgcctt    960
tgaaagcaac aattttattt acttcttgac ggtccaaagg gaaactctag atgctcagac   1020
ttttcacaca gaataatca ggttctgttc cataaactct ggattgcatt cctacatgga   1080
aatgcctctg gagtgtattc tcacagaaaa gagaaaaaag agatccacaa agaaggaagt   1140
gtttaatata cttcaggctg cgtatgtcag caagcctggg gcccagcttg ctagacaaat   1200

```
aggagccagc ctgaatgatg acattctttt cggggtgttc gcacaaagca agccagattc    1260
tgccgaacca atggatcgat ctgccatgtg tgcattccct atcaaatatg tcaacgactt    1320
cttcaacaag atcgtcaaca aaaacaatgt gagatgtctc cagcattttt acggacccaa    1380
tcatgagcac tgctttaata ggacacttct gagaaattca tcaggctgtg aagcgcgccg    1440
tgatgaatat cgaacagagt ttaccacagc tttgcagcgc gttgacttat tcatgggtca    1500
attcagcgaa gtcctcttaa catctatatc caccttcatt aaaggagacc tcaccatagc    1560
taatcttggg acatcagagg gtcgcttcat gcaggttgtg gtttctcgat caggaccatc    1620
aaccccctcat gtgaattttc tcctggactc ccatccagtg tctccagaag tgattgtgga    1680
gcatacatta aaccaaaatg ctacacact ggttatcact gggaagaaga tcacgaagat    1740
cccattgaat ggcttgggct gcagacattt ccagtcctgc agtcaatgcc tctctgcccc    1800
acccttgtt cagtgtggct ggtgccacga caaatgtgtg cgatcggagg aatgcctgag    1860
cgggacatgg actcaacaga tctgtctgcc tgcaatctac aaggttttcc caaatagtgc    1920
acccccttgaa ggagggacaa ggctgaccat atgtggctgg gactttggat tcggaggaa    1980
taataaattt gatttaaaga aaactagagt tctccttgga aatgagagct gcaccttgac    2040
tttaagtgag agcacgatga atacattgaa atgcacagtt ggtcctgcca tgaataagca    2100
tttcaatatg tccataatta tttcaaatgg ccacgggaca acacaataca gtacattctc    2160
ctatgtggat cctgtaataa caagtatttc gccgaaatac ggtcctatgg ctggtggcac    2220
tttacttact ttaactggaa attacctaaa cagtgggaat tctagacaca tttcaattgg    2280
tggaaaaaca tgtactttaa aaagtgtgtc aaacagtatt cttgaatgtt ataccccagc    2340
ccaaaccatt tcaactgagt ttgctgttaa attgaaaatt gacttagcca accgagagac    2400
aagcatcttc agttaccgtg aagatcccat tgtctatgaa attcatccaa ccaaatcttt    2460
tattagtact tggtggaaag aacctctcaa cattgtcagt tttctatttt gctttgccag    2520
tggtgggagc acaataacag gtgttgggaa aaacctgaat tcagttagtg tcccgagaat    2580
ggtcataaat gtgcatgaag caggaaggaa ctttacagtg gcatgtcaac atcgctctaa    2640
ttcagagata atctgttgta ccactccttc cctgcaacag ctgaatctgc aactccccct    2700
gaaaaccaaa gccttttca tgttagatgg gatccttttcc aaatactttg atctcattta    2760
tgtacataat cctgtgttta agcctttga aaagccagtg atgatctcaa tgggcaatga    2820
aaatgtactg gaaattaagg gaaatgatat tgaccctgaa gcagttaaag gtgaagtgtt    2880
aaaagttgga aataagagct gtgagaatat acacttacat tctgaagccg ttttatgcac    2940
ggtccccaat gacctgctga aattgaacag cgagctaaat atagagtgga agcaagcaat    3000
ttcttcaacc gtccttggaa aagtaatagt tcaaccagat cagaatttca caggattgat    3060
tgctggtgtt gtctcaatat caacagcact gttattacta cttgggtttt tcctgtggct    3120
gaaaaagaga aagcaaatta agatctgggc agtgaatta gttcgctacg atgcaagagt    3180
acacactcct catttggata ggcttgtaag tgcccgaagt gtaagcccaa ctacagaaat    3240
ggtttcaaat gaatctgtag actaccgagc tactttttcca gaagatcagt ttcctaattc    3300
atctcagaac ggttcatgcc gacaagtgca gtatcctctg acagacatgt cccccatcct    3360
aactagtggg gactctgata tatccagtcc attactgcaa aatactgtcc acattgacct    3420
cagtgctcta aatccagagc tggtccaggc agtgcagcat gtagtgattg ggcccagtag    3480
cctgattgtg catttcaatg aagtcatagg aagagggcat tttggttgtg tatatcatgg    3540
gactttgttg gacaatgatg gcaagaaaat tcactgtgct gtgaaatcct tgaacagaat    3600
```

```
cactgacata ggagaagttt cccaatttct gaccgaggga atcatcatga aagattttag    3660
tcatcccaat gtcctctcgc tcctgggaat ctgcctgcga agtgaagggt ctccgctggt    3720
ggtcctacca tacatgaaac atggagatct tcgaaatttc attcgaaatg agactcataa    3780
tccaactgta aaagatctta ttggcttttgg tcttcaagta gccaaaggca tgaaatatct    3840
tgcaagcaaa aagtttgtcc acagagactt ggctgcaaga aactgtatgc tggatgaaaa    3900
attcacagtc aaggttgctg attttggtct tgccagagac atgtatgata agaatacta    3960 tagtgtacac aacaaaacag gtgcaaagct gccagtgaag tggatggctt tggaaagtct    4020
gcaaactcaa aagtttacca ccaagtcaga tgtgtggtcc tttggcgtgc tcctctggga    4080
gctgatgaca agaggagccc caccttatcc tgacgtaaac acctttgata taactgttta    4140
cttgttgcaa gggagaagac tcctacaacc cgaatactgc ccagacccct tatatgaagt    4200
aatgctaaaa tgctggcacc ctaaagccga aatgcgccca tccttttctg aactggtgtc    4260
ccggatatca gcgatcttct ctactttcat tggggagcac tatgtccatg tgaacgctac    4320
ttatgtgaac gtaaaatgtg tcgctccgta tccttctctg ttgtcatcag aagataacgc    4380
tgatgatgag gtggacacac gaccagcctc cttctgggag acatcatagt gctagtacta    4440
tgtcaaagca acagtccaca ctttgtccaa tggttttttc actgcctgac ctttaaaagg    4500
ccatcgatat tctttgctct tgccaaaatt gcactattat aggacttgta ttgttattta    4560
aattactgga ttctaaggaa tttcttatct gacagagcat cagaaccaga ggcttggtcc    4620
cacaggccac ggaccaatgg cctgcagccg tgacaacact cctgtcatat tggagtccaa    4680
aacttgaatt ctgggttgaa tttttttaaaa atcaggtacc acttgatttc atatgggaaa    4740
ttgaagcagg aaatattgag ggcttcttga tcacagaaaa ctcagaagag atagtaatgc    4800
tcaggacagg agcggcagcc ccagaacagg ccactcattt agaattctag tgtttcaaaa    4860 cactttgtg tgttgtatgg tcaataacat ttttcattac tgatggtgtc attcacccat    4920
taggtaaaca ttccctttta aatgtttgtt tgttttttga gacaggatct cactctgttg    4980
ccagggctgt agtgcagtgg tgtgatcata gctcactgca acctccacct cccaggctca    5040
agcctcccga atagctggga ctacaggcgc acaccaccat ccccggctaa ttttgtatt    5100 ttttgtagag acggggtttt gccatgttgc caaggctggt ttcaaactcc tggactcaag    5160
aaatccaccc acctcagcct cccaaagtgc taggattaca ggcatgagcc actgcgccca    5220
gcccttataa attttttgtat agacattcct ttggttggaa gaatatttat aggcaataca    5280
gtcaaagttt caaaatagca tcacacaaaa catgtttata aatgaacagg atgtaatgta    5340
catagatgac attaagaaaa tttgtatgaa ataatttagt catcatgaaa tatttagttg    5400
tcatataaaa acccactgtt tgagaatgat gctactctga tctaatgaat gtgaacatgt    5460
agatgttttg tgtgtatttt tttaaatgaa aactcaaaat aagacaagta atttgttgat    5520 aaatatttt aaagataact cagcatgttt gtaaagcagg atacatttta ctaaaaggtt    5580
cattggttcc aatcacagct cataggtaga gcaaagaaag ggtggatgga ttgaaaagat    5640
tagcctctgt ctcggtggca ggttcccacc tcgcaagcaa ttggaaacaa aacttttggg    5700 gagtttttatt ttgcattagg gtgtgtttta tgttaagcaa aacatacttt agaaacaaat    5760
gaaaaaggca attgaaaatc ccagctattt cacctagatg gaatagccac cctgagcaga    5820
actttgtgat gcttcattct gtggaatttt gtgcttgcta ctgtatagtg catgtggtgt    5880
aggttactct aactggtttt gtcgacgtaa acatttaaag tgttatattt tttataaaaa    5940
```

| | | | | | | |
|---|---|---|---|---|---|---|
| tgtttatttt | taatgatatg | agaaaaattt | tgttaggcca | caaaaacact | gcactgtgaa | 6000 |
| cattttagaa | aaggtatgtc | agactgggat | taatgacagc | atgattttca | atgactgtaa | 6060 |
| attgcgataa | ggaaatgtac | tgattgccaa | tacaccccac | cctcattaca | tcatcaggac | 6120 |
| ttgaagccaa | gggttaaccc | agcaagctac | aaagagggtg | tgtcacactg | aaactcaata | 6180 |
| gttgagtttg | gctgttgttg | caggaaaatg | attataacta | aaagctctct | gatagtgcag | 6240 |
| agacttacca | gaagacacaa | ggaattgtac | tgaagagcta | ttacaatcca | aatattgccg | 6300 |
| tttcataaat | gtaataagta | atactaattc | acagagtatt | gtaaatggtg | gatgacaaaa | 6360 |
| gaaaatctgc | tctgtggaaa | gaaagaactg | tctctaccag | ggtcaagagc | atgaacgcat | 6420 |
| caatagaaag | aactcgggga | aacatcccat | caacaggact | acacacttgt | atatacattc | 6480 |
| ttgagaacac | tgcaatgtga | aaatcacgtt | tgctatttat | aaacttgtcc | ttagattaat | 6540 |
| gtgtctggac | agattgtggg | agtaagtgat | tcttctaaga | attagatact | tgtcactgcc | 6600 |
| tatacctgca | gctgaactga | atggtacttc | gtatgttaat | agttgttctg | ataaatcatg | 6660 |
| caattaaagt | aaagtgatgc | aacatcttgt | aaaaaaaaaa | aaaaaaaaaa | | 6710 |